US010568351B2

(12) United States Patent
Jackson et al.

(10) Patent No.: US 10,568,351 B2
(45) Date of Patent: *Feb. 25, 2020

(54) REBAUDIOSIDE A AND STEVIOSIDE WITH IMPROVED SOLUBILITIES

(71) Applicant: SWEET GREEN FIELDS USA LLC, Bellingham, WA (US)

(72) Inventors: Mel Clinton Jackson, Waikoioa, HI (US); Samuel Mel Jackson, Honolulu, HI (US); Dean Edward Francis, Blaine, WA (US)

(73) Assignee: Sweet Green Fields USA LLC, Bellingham, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/446,204

(22) Filed: Jun. 19, 2019

(65) Prior Publication Data
US 2019/0297934 A1 Oct. 3, 2019

Related U.S. Application Data

(63) Continuation of application No. 14/739,887, filed on Jun. 15, 2015, now Pat. No. 10,357,052.

(60) Provisional application No. 62/012,936, filed on Jun. 16, 2014.

(51) Int. Cl.
| *A23L 33/125* | (2016.01) |
| *A23L 5/00* | (2016.01) |
| *A23L 29/30* | (2016.01) |
| *A23L 27/30* | (2016.01) |
| *A23L 2/02* | (2006.01) |
| *A23L 2/60* | (2006.01) |
| *A23C 9/13* | (2006.01) |
| *C07H 1/08* | (2006.01) |
| *C07H 15/256* | (2006.01) |
| *C07H 15/24* | (2006.01) |
| *A23L 7/00* | (2016.01) |
| *A23L 21/00* | (2016.01) |

(52) U.S. Cl.
CPC .......... *A23L 33/125* (2016.08); *A23C 9/1307* (2013.01); *A23L 2/02* (2013.01); *A23L 2/60* (2013.01); *A23L 5/00* (2016.08); *A23L 27/30* (2016.08); *A23L 27/34* (2016.08); *A23L 27/36* (2016.08); *A23L 29/30* (2016.08); *C07H 1/08* (2013.01); *C07H 15/24* (2013.01); *C07H 15/256* (2013.01); *A23L 7/00* (2016.08); *A23L 21/00* (2016.08); *A23V 2002/00* (2013.01); *A23V 2200/00* (2013.01); *A23V 2200/132* (2013.01); *A23V 2250/262* (2013.01); *A23V 2250/61* (2013.01)

(58) Field of Classification Search
None
See application file for complete search history.

(56) References Cited

U.S. PATENT DOCUMENTS

| 3,529,602 | A | 9/1970 | Hind et al. |
| 3,703,177 | A | 11/1972 | Hind et al. |
| 4,079,742 | A | 3/1978 | Norman et al. |
| 4,082,858 | A | 4/1978 | Morita et al. |
| 4,335,889 | A | 6/1982 | Cather, Jr. et al. |
| 4,361,697 | A | 11/1982 | Dobberstein et al. |
| 4,612,942 | A | 9/1986 | Dobberstein et al. |
| 4,892,938 | A | 1/1990 | Giovanetto |
| 5,112,610 | A | 5/1992 | Kienle |
| 5,962,678 | A | 10/1999 | Payzant et al. |
| 5,972,120 | A | 10/1999 | Kutowy et al. |
| 6,096,870 | A | 8/2000 | Mozaffar et al. |
| 7,238,379 | B2 | 7/2007 | Lang |
| 7,923,552 | B2 | 4/2011 | Jackson et al. |
| PP22,593 | P3 | 3/2012 | Garnighian |
| 8,153,563 | B2 | 4/2012 | Morgan et al. |
| 8,257,948 | B1 | 9/2012 | Markosyan |
| PP23,164 | P3 | 11/2012 | Britos |
| 8,318,459 | B2 | 11/2012 | Markosyan |
| 8,367,138 | B2 | 2/2013 | Prakash et al. |
| 2003/0138538 | A1 | 7/2003 | Kitazume et al. |
| 2003/0139610 | A1 | 7/2003 | Khare et al. |
| 2006/0083838 | A1 | 4/2006 | Jackson et al. |
| 2006/0134292 | A1 | 6/2006 | Abelyan et al. |
| 2006/0142555 | A1 | 6/2006 | Jonnala et al. |
| 2007/0003679 | A1 | 1/2007 | Shimizu et al. |
| 2007/0082103 | A1 | 4/2007 | Magomet et al. |
| 2007/0116823 | A1 | 5/2007 | Prakash et al. |
| 2007/0116835 | A1 | 5/2007 | Prakash et al. |
| 2007/0128311 | A1 | 6/2007 | Prakash et al. |
| 2007/0292582 | A1 | 12/2007 | Prakash et al. |
| 2008/0026111 | A1 | 1/2008 | Bellody et al. |

(Continued)

FOREIGN PATENT DOCUMENTS

| AU | 2004/202670 | 1/2005 |
| CA | 2 185 496 | 3/1998 |

(Continued)

OTHER PUBLICATIONS

Communication pursuant to Article 94(3) EPC dated Feb. 27, 2018 in EP application No. 15 735 775.7.

(Continued)

*Primary Examiner* — Nikki H. Dees
*Assistant Examiner* — Amber M Cox
(74) *Attorney, Agent, or Firm* — Michael X. Ye; Morris, Manning & Martin, LLP

(57) ABSTRACT

The invention describes sweetening compositions and methods to prepare sweetening compositions containing steviol glycosides, salts, and other natural or synthetic sweeteners with improved solubilities and sensory profiles.

19 Claims, 13 Drawing Sheets

(56) References Cited

U.S. PATENT DOCUMENTS

| | | |
|---|---|---|
| 2008/0300402 A1 | 12/2008 | Yang et al. |
| 2010/0099857 A1 | 4/2010 | Evans |
| 2010/0112156 A1 | 5/2010 | Abelyan et al. |
| 2010/0137569 A1 | 6/2010 | Prakash et al. |
| 2010/0316782 A1 | 12/2010 | Shi et al. |
| 2011/0195161 A1 | 8/2011 | Upreti et al. |
| 2012/0058236 A1 | 3/2012 | Fosdick et al. |
| 2012/0058247 A1 | 3/2012 | Shi |
| 2012/0090062 P1 | 4/2012 | Britos |
| 2012/0090063 P1 | 4/2012 | Britos |
| 2012/0184500 A1 | 7/2012 | Goralczyk et al. |
| 2012/0214751 A1 | 8/2012 | Markosyan |
| 2012/0214752 A1 | 8/2012 | Markosyan |
| 2012/0269954 A1 | 10/2012 | Bridges et al. |
| 2012/0282389 A1 | 11/2012 | Purkayastha et al. |
| 2012/0301589 A1 | 11/2012 | Markosyan |
| 2013/0071537 A1 | 3/2013 | Shi et al. |
| 2013/0274351 A1 | 10/2013 | Markosyan et al. |

FOREIGN PATENT DOCUMENTS

| | | |
|---|---|---|
| CN | 1192447 | 9/1998 |
| CN | 1238341 | 12/1999 |
| CN | 1243835 | 2/2000 |
| CN | 101220062 | 7/2001 |
| CN | 1078217 C | 1/2002 |
| CN | 1535607 | 10/2004 |
| CN | 101062078 | 10/2007 |
| CN | 101200480 | 6/2008 |
| CN | 101330833 | 12/2008 |
| CN | 101472487 | 7/2009 |
| CN | 101662955 | 3/2010 |
| CN | 101801177 | 8/2010 |
| CN | 101854814 | 10/2010 |
| EP | 2 215 914 | 8/2010 |
| EP | 2 415 358 | 2/2012 |
| EP | 2 428 123 | 3/2012 |
| EP | 2 456 450 | 5/2012 |
| EP | 2 457 450 | 5/2012 |
| EP | 2 460 419 | 6/2012 |
| EP | 2 486 806 | 8/2012 |
| FR | 2 968 170 | 6/2012 |
| JP | 52-023100 | 2/1977 |
| JP | 52-062300 | 5/1977 |
| JP | 54-041898 | 4/1979 |
| JP | 54-041899 | 4/1979 |
| JP | 54-041900 | 4/1979 |
| JP | 55-092400 | 7/1980 |
| JP | 56-121453 | 9/1981 |
| JP | 56-121454 | 9/1981 |
| JP | 56-121455 | 9/1981 |
| JP | 57-086264 | 5/1982 |
| JP | 58-101660 | 6/1983 |
| JP | 59120073 | 11/1984 |
| JP | 62-146599 | 6/1987 |
| JP | 63-173531 | 7/1988 |
| JP | 2-261359 | 10/1990 |
| JP | 6-192283 | 7/1994 |
| JP | 7-143860 | 6/1995 |
| JP | 7-177862 | 7/1995 |
| JP | 08-000214 | 1/1996 |
| JP | 08-325156 | 10/1996 |
| JP | 11-243906 | 9/1999 |
| JP | 2002-45145 | 2/2002 |
| JP | 2002-262822 | 9/2002 |
| JP | 2004-344071 | 12/2004 |
| JP | 2012-005483 | 1/2012 |
| JP | 2012-090629 | 5/2012 |
| KR | 1996-0016568 | 12/1996 |
| KR | 2004-0026747 | 4/2004 |
| WO | 00/49895 | 8/2000 |
| WO | 2003/003994 | 1/2003 |
| WO | 03-033097 | 4/2003 |
| WO | 06-038221 | 4/2006 |
| WO | 06-045023 | 4/2006 |
| WO | 06-072921 | 7/2006 |
| WO | 2006095366 | 9/2006 |
| WO | 2007/061810 | 5/2007 |
| WO | 2007/061898 | 5/2007 |
| WO | 2007061795 | 5/2007 |
| WO | 2008/057968 | 5/2008 |
| WO | 2008/091547 | 7/2008 |
| WO | 2008147725 | 12/2008 |
| WO | 2013096420 | 12/2008 |
| WO | 2009086043 | 7/2009 |
| WO | 2009/140394 | 11/2009 |
| WO | 2010/150930 | 12/2010 |
| WO | 2011046423 | 4/2011 |
| WO | 2011/059954 | 5/2011 |
| WO | 2011/094423 | 8/2011 |
| WO | 2011/161027 | 12/2011 |
| WO | 2012006728 | 1/2012 |
| WO | 2012/031879 | 3/2012 |
| WO | 2012/006742 | 5/2012 |
| WO | 2012/057575 | 5/2012 |
| WO | 2012/068457 | 5/2012 |
| WO | 2012/073121 | 6/2012 |
| WO | 2012/082677 | 6/2012 |
| WO | 2012/089861 | 7/2012 |
| WO | 2012/102769 | 8/2012 |
| WO | 2012/108894 | 8/2012 |
| WO | 2012/109506 | 8/2012 |
| WO | 2012/109585 | 8/2012 |
| WO | 2012/112177 | 8/2012 |
| WO | 2012/112180 | 8/2012 |
| WO | 2012/134502 | 10/2012 |
| WO | 2012/153339 | 11/2012 |
| WO | 2012/166163 | 12/2012 |
| WO | 2012/166164 | 12/2012 |
| WO | 2013/036366 | 3/2013 |
| WO | 2013058870 | 4/2013 |
| WO | 2013123281 | 8/2013 |
| WO | 2014052457 | 3/2014 |
| WO | 2014152791 | 9/2014 |
| WO | 2014185931 | 11/2014 |

OTHER PUBLICATIONS

International Search Report and Written Opinion from PCT/182015/053685, dated Sep. 24, 2015, 14 pages.

International Search Report and Written Opinion from related International Application PCT/US2015/036098, dated Sep. 24, 2015, 11 pages.

Kasai, et al., "Synthesis of Sweet Diterpene-Glycoside of Leaves of Stevia: rebaudiosides-A, -D, -E and their relating glycosides as well as Relationship between their Sweetness and Chemical Structure"; Journal of Chemical Society of Japan, No. 5, 1981; pp. 726-735.

Kinghorn, et al., "Studies to Identify, Isolate, Develop and test Naturally Occurring D Noncariogenic Sweeteners that May be Used as Dietary Sucrose Substitutes", Government Reports and Announcements Index, United States, Chemical Abstracts, 1985, 35 pages.

Kolb, et al., "Analysis of Sweet Diterpene Glycosides from Stevia rebaudiana: Improved HPLC Method", Journal of Agricultural Food Chemistry, vol. 49, 2001, pp. 4538-4541.

Ohtani, et al., "Methods to Improve the Taste of the Sweet Principles of Stevia Rebaudiana", D Stevia, The Genus *Stevia*, Edited by A. Douglas Kinghorn, CRC Press, Print ISBN 978-0-415-26830-1, 2001, pp. 138-159.

Sharma, et al., "Chemistry and in vivo profile of ent-kaurene glycosides of Stevia rebaudianna Bertoni—An overview", Natural Product Radiance, vol. 8(2), 2009, pp. 181-189.

Tanaka, "Improvement of Taste of Naturel Sweeteners", Pure & Appl. Chem., vol. 69, No. 4, 1997, pp. 675-683.

Prakash, et al., "Development of rebiana, a natural, non-caloric sweetener", Food and Chemical Toxicology, No. 46(7), 2008, pp. S75-S82.

Abou-Arab, et al., "Physico-chemical assessment of natural sweeteners steviosides produced from *Stevia rebaudiana bertoni* plant", African J. Food Sci., May 2010, vol. 4, No. 5, pp. 269-281.

Brandle, et al., "Steviol glycoside biosynthesis", Phytochemistry. 2007, No. 68(14), pp. 1855-1863.

(56) References Cited

OTHER PUBLICATIONS

Crammer, B. and Ikan, R. "Progress in the chemistry and properties of rebaudiosides," In Developments in Sweeteners-3, T.H. Grenby (ed), Elsevier Applied Science, London, pp. 45-64 (1987).
Makapugay, et al., "Improved high-performance liquid chromatographic separation of the Stevia rebaudiana sweet diterpene glycosides using linear gradient elution", Journal of Chromatography, No. 283, 1984, pp. 390-395.
Serajuddin, "Salt Formation to Improve Drug Solubility", Advance Drug Delivery Reviews, No. 59, 2007, pp. 603-616.
Shibata, et al. Glucosylation of Steviol and Steviol-Glucosides in Extracts from Stevia rebaudiana Bertoni, Plant Physiol. 1991, vol. 95, pp. 152-156.
Upreti, et al. "Solubility Enhancement of Steviol Glycosides and Characterization of Their Inclusion Complex with Gamma-Cyclodextrin", Int. J. Mol. Sci. Nov. 2011, vol. 12, pp. 7529-7553.
International Search Report from related PCT Application PCT/IB2011/002636, dated Apr. 12, 2012, 3 pages.
International Search Report from PCT/US2012/029613, dated Feb. 1, 2013, 3 pages.
International Preliminary Report on Patentability from related PCT ApplicationPCT/IB2011/002636, dated Feb. 26, 2013, 5 pages.
International Search Report from PCT/US2008/000700, dated Jul. 31, 2008, 5 pages.
International Search Report from PCT/IB201 0/003045, dated May 5, 2011, 4 pages.
International Search Report and Written Opinion from PCT/IB2011/003351, dated Jul. 26, 2012, 5 pages.
International Search Report and Written Opinion from PCT/IB2010/001636, dated Dec. 2, 2010, 4 pages.
U.S. Appl. No. 14/739,887, filed Jun. 15, 2015.
U.S. Appl. No. 62/012,936, filed Jun. 16, 2014.

Effect of Amount NaOH addition on relative % RB from Various RA purity starts A after 18hr incubation at 90C

| mls 20% NaOH add | g NaOH Add | g glucose potentially product | % glucose in 300ppm | %NaOH to Stev | pH | %RA | %RB | %RC | %STV | %SB | pH | %RA | %RB | %RC | %STV | %SB | pH | %RA | %RB | %RC | %STV | %SB |
|---|---|---|---|---|---|---|---|---|---|---|---|---|---|---|---|---|---|---|---|---|---|---|
| | | | | | | 4g RA50 | | | | | | 4g RA80 | | | | | | 4g RA97 | | | | |
| 0 | 0 | 0 | 0 | 0 | 5.9 | 53.16 | 0.45 | 5.42 | 36.37 | 0.19 | 5.8 | 81.9 | 2.2 | 3.5 | 3.9 | 0.2 | 5.7 | 97.4 | 2.9 | 0.1 | 0.1 | 0.0 |
| 0.0625 | 0.0125 | 0.0563125 | 0.000423438 | 0.33125 | 6 | 43.3 | 6.3 | 4.7 | 36.6 | 4.3 | 5.8 | 73.5 | 9.9 | 3.8 | 6.9 | 0.9 | 5.9 | 85.8 | 11.8 | 0.2 | 0.3 | 0.0 |
| 0.125 | 0.025 | 0.112625 | 0.000846875 | 0.625 | 6.3 | 40.5 | 8.7 | 4.5 | 34.6 | 6.5 | 6.3 | 68.9 | 15.2 | 2.8 | 6.8 | 1.3 | 6.3 | 79.3 | 18.1 | 0.3 | 0.4 | 0.0 |
| 0.25 | 0.05 | 0.22525 | 0.01689375 | 1.25 | 6.8 | 34.4 | 15.0 | 4.0 | 29.5 | 11.1 | 6.6 | 63.2 | 24.9 | 2.3 | 5.1 | 2.1 | 6.7 | 67.7 | 28.8 | 0.3 | 0.4 | 0.1 |
| 0.3125 | 0.0625 | 0.2815625 | 0.021117188 | 1.5625 | 6.9 | 32.4 | 17.1 | 3.8 | 28.1 | 13.0 | 6.8 | 60.2 | 28.8 | 2.2 | 4.9 | 2.5 | 6.8 | 63.4 | 34.2 | 0.3 | 0.4 | 0.1 |
| 0.375 | 0.075 | 0.337875 | 0.025340625 | 1.875 | 7 | 29.5 | 19.7 | 3.5 | 25.7 | 15.1 | 6.9 | 50.5 | 34.4 | 2.1 | 4.5 | 3.0 | 7.0 | 57.8 | 39.2 | 0.3 | 0.3 | 0.1 |
| 0.4375 | 0.0875 | 0.3941875 | 0.029564063 | 2.1875 | 7.1 | 26.5 | 22.6 | 3.3 | 23.2 | 17.4 | 6.9 | 47.3 | 37.5 | 1.9 | 4.4 | 3.2 | 7.1 | 53.8 | 44.4 | 0.3 | 0.2 | 0.1 |
| 0.5 | 0.1 | 0.45075 | 0.033788 | 2.5 | | | | | | | | | | | | | | | | | | |
| 0.5625 | 0.1125 | 0.5068125 | 0.038010938 | 2.8125 | 7.3 | 21.7 | 27.8 | 2.8 | 19.1 | 21.5 | 7.2 | 36.2 | 48.3 | 1.8 | 3.4 | 4.2 | 7.3 | 40.9 | 55.4 | 0.2 | 0.3 | 0.1 |
| 0.625 | 0.125 | 0.563125 | 0.042234375 | 3.125 | 7.4 | 19.4 | 29.5 | 2.7 | 17.8 | 23.0 | 7.3 | 31.8 | 53.7 | 1.5 | 3.1 | 4.7 | 7.4 | 36.3 | 62.1 | 0.1 | 0.3 | 0.1 |

FIG. 1

| Sample (Q.S to 500ml) Sample description | Tester #1 Ov Like | Tester #2 Ov Like | Tester #3 Ov Like | Tester #4 Ov Like | Tester #5 Ov Like | Tester #6 Ov Like | Tester #7 Ov Like | Tester #8 Ov Like | Tester #9 Ov Like | Tester #10 Ov Like | Tester #11 Ov Like |
|---|---|---|---|---|---|---|---|---|---|---|---|
| 799 50% S R Lemon & Lime CSD + 235ppm RA extract | 9 | 7 | | 4 | 5 | 7 | 6 | 6 | 3 | 9 | 4 |
| 236 50% S R Lemon & Lime CSD + 235ppm ABH-97 | 9 | 3 | | 6 | 7 | 3 | 5.5 | 4 | 8 | 7 | 6 |

| Sample (Q.S to 500ml) Sample description | Tester #1 Sweetness | Tester #2 sweetness | Tester #3 sweetness | Tester #4 sweetness | Tester #5 sweetness | Tester #6 sweetness | Tester #7 sweetness | Tester #8 sweetness | Tester #9 sweetness | Tester #10 sweetness | Tester #11 Sweet |
|---|---|---|---|---|---|---|---|---|---|---|---|
| 799 50% S R Lemon & Lime CSD + 235ppm RA extract | 7 | 8 | | 4 | 5 | 8 | 7 | 7 | 5 | 9 | 6 |
| 236 50% S R Lemon & Lime CSD + 235ppm ABH-97 | 7 | 8 | | 4 | 7 | 8 | 5 | 6 | 8 | 9 | 7.5 |

| Sample (Q.S to 500ml) Sample description | Tester #1 Bitterness | Tester #2 Bitter | Tester #3 Bitterness | Tester #4 Bitterness | Tester #5 Bitterness | Tester #6 Bitterness | Tester #7 Bitterness | Tester #8 Bitterness | Tester #9 Bitterness | Tester #10 Bitterness | Tester #11 Bitter |
|---|---|---|---|---|---|---|---|---|---|---|---|
| 799 50% S R Lemon & Lime CSD + 235ppm RA extract | 3 | 3 | | 3 | 3 | 7 | 5.6 | 4 | 4 | 1 | 3.5 |
| 236 50% S R Lemon & Lime CSD + 235ppm ABH-97 | 2 | | | 4 | 6 | 3 | 5.3 | 5 | 4 | 2 | 3.5 |

| Sample (Q.S to 500ml) Sample description | Tester #1 Sugar-like | Tester #2 Sugar Likeness | Tester #3 Sugar Likeness | Tester #4 Sugar Likeness | Tester #5 Sugar Likeness | Tester #6 Sugar Likeness | Tester #7 Sugar Likeness | Tester #8 Sugar Likeness | Tester #9 Sugar Likeness | Tester #10 Sugar Likeness | Tester #11 Sugar likeness |
|---|---|---|---|---|---|---|---|---|---|---|---|
| 799 50% S R Lemon & Lime CSD + 235ppm RA extract | 5 | 8 | | 5 | 5 | 8 | 7 | 5 | 5 | 6 | 4 | 6.5 |
| 236 50% S R Lemon & Lime CSD + 235ppm ABH-97 | 7 | 8 | | 4 | 5 | 6 | 6 | 6 | 7 | 7 | 6 | 5.3 |

| Sample (Q.S to 500ml) Sample description | Tester #1 MD | Tester #2 MD | Tester #3 MD | Tester #4 MD | Tester #5 MD | Tester #6 MD | Tester #7 MD | Tester #8 MD | Tester #9 MD | Tester #10 MD | |
|---|---|---|---|---|---|---|---|---|---|---|---|
| 799 50% S R Lemon & Lime CSD + 235ppm RA extract | 6 | 6 | | 4 | 5 | 3 | 6 | 4 | 3 | 2 | 5 |
| 236 50% S R Lemon & Lime CSD + 235ppm ABH-97 | 4 | 6 | | 2 | 5 | 3 | 7 | 7 | 8 | 4 | 4 |

FIG. 5

Anova: Single Factor

SUMMARY OV Like

| Groups | Count | Sum | Average | Variance | F | P-value | F crit |
|---|---|---|---|---|---|---|---|
| Row 1 | 11.00 | 67.00 | 6.09 | 3.89 | 0.32 | 0.58 | 4.35 |
| Row 2 | 11.00 | 71.50 | 6.50 | 1.85 | | | |

SUMMARY SWEETNESS

| Groups | Count | Sum | Average | Variance | F | P-value | F crit |
|---|---|---|---|---|---|---|---|
| Row 1 | 11.00 | 72.00 | 6.55 | 2.27 | 0.42 | 0.52 | 4.35 |
| Row 2 | 11.00 | 76.50 | 6.95 | 2.12 | | | |

SUMMARY BITTERNESS

| Groups | Count | Sum | Average | Variance | F | P-value | F crit |
|---|---|---|---|---|---|---|---|
| Row 1 | 11.00 | 38.10 | 3.46 | 3.06 | 0.01 | 0.93 | 4.35 |
| Row 2 | 11.00 | 38.80 | 3.53 | 2.35 | | | |

SUMMARY SUGAR LIKE

| Groups | Count | Sum | Average | Variance | F | P-value | F crit |
|---|---|---|---|---|---|---|---|
| Row 1 | 11.00 | 62.50 | 5.68 | 2.51 | 0.51 | 0.49 | 4.35 |
| Row 2 | 11.00 | 67.30 | 6.12 | 1.63 | | | |

SUMMARY

| Groups | Count | Sum | Average | Variance | F | P-value | F crit |
|---|---|---|---|---|---|---|---|
| Row 1 | 10 | 44 | 4.4 | 2.04444 | 0.61832 | 0.4419 | 4.413873 |
| Row 2 | 10 | 50 | 5 | 3.77778 | | | |

Anova: Single Factor

FIG. 6

| Sample | Sample (Q.S to 500ml) description | Sweetness Average | Bitterness Average | Sugar Like Average | Mouth drying Average | Overall Like Average |
|---|---|---|---|---|---|---|
| 799 | 50% S.R Lemon & Lime CSD + 235ppm RA extract | 6.55 | 3.46 | 5.68 | 4.4 | 6.09 |
| 236 | 50% S.R Lemon & Lime CSD + 235ppm ABH-97 | 6.95 | 3.53 | 6.12 | 5 | 6.50 |

FIG. 7

REBAUDIOSIDE A AND STEVIOSIDE WITH IMPROVED SOLUBILITIES

This application is a continuation of U.S. patent application Ser. No. 14/739,887, filed Jun. 15, 2015, which claims benefit to U.S. Provisional Patent Application Ser. No. 62/012,936, filed Jun. 16, 2014, the contents of which is incorporated herein by reference in its entirety.

FIELD

The present invention discloses sweetening compositions containing steviol glycosides, salts, and other natural or synthetic sweeteners with improved solubilities and sensory profiles.

BACKGROUND OF THE INVENTION

The stems and leaves of *Stevia rebaudiana* contain a group of diterpene glycosides, called "steviol glycosides", some of which are up to 400 times sweeter than table sugar (sucrose), depending upon the sucrose equivalence (defined below) required for a given food, beverage, or other comestible. Many steviol glycosides have been isolated and identified, and include, but are not limited to: rebaudioside A ("Reb A" or "RA"), rebaudioside B ("Reb B" or "RB"), stevioside ("STV"), steviol bioside ("STB"), rebaudiosides C, D, E, and F, rubusoside, and dulcoside A. All of these compounds are sweet; however, at commonly used sucrose equivalencies, all but pure rebaudioside A also have a bitter in-mouth taste (taste while a test substance is in the buccal cavity) and bitter aftertaste (lingering taste after swallowing or expectoration of the test substance). Reb A has a clean sweet taste and, at purities greater than 99% and at commonly used sucrose equivalencies, has none of the in-mouth bitterness and bitter aftertaste associated with the other steviol glycosides. Reb A can be produced in various purities using, inter alia, the process described by Jackson in U.S. patent application Ser. No. 11/252,430 (U.S. published application no. 2006/0083838, issued as U.S. Pat. No. 7,923,552) which is fully incorporated hereby by reference).

Blends of various purities of rebaudioside A can be used as sweeteners. The higher the RA content of a sweetener, the more expensive the sweetener is. Blending various purities of rebaudioside A produces sweeteners at selling prices corresponding to the RA purity of the ingredients: the higher the RA purity of the ingredients, the higher the selling price of the blended sweetener.

Liquid sweeteners are required for beverage production and for many food products at commercial scale. Some countries have a strong preference for liquid table top sweeteners, e.g., South American and Asian countries. Non-caloric and low caloric natural, "high intensity" sweeteners are in high demand for use in non-caloric or reduced-caloric foods and beverages, but widespread adoption of sweeteners containing RA and/or STV has been hindered by two factors: (1) the solubility of Reb A and STV are proportional to the Reb A or STV content of the sweetener, and (2) the sensory profile of steviol glycosides differs significantly from that of sucrose in, inter alia, slow temporal decay of sweetness, and "thin" mouth feel; moreover, purities of Reb A lower than RA97 and any purity of STV typically have a bitter aftertaste at sucrose equivalencies used in foods and beverages. This means that the more soluble a known Reb A or STV sweetener is, the worse it can taste. The problems with solubility of known Reb A and STV compositions are described have been disclosed in the art (Prakash et al, "Development of rebiana, a natural, non-caloric sweetener", Food and Chemical Toxicology", 46:7, Suppl., July 2008, Pages S75-S82.

RA50 (RA50 is a product comprising >50% RA, and >95% total steviol glycosides) powder dissolves easily in water at 25° C., but the solubility of RA97 (RA97 is a high purity RA product comprising >97% RA) under the same conditions is only 0.8%. The higher the purity Reb A or STV, the faster it precipitates out of solution. A concentration of RA97 any higher than 0.8% rapidly precipitates out of solution. High purity STV also exhibits a similar phenomenon of very low solubility, and rapid precipitation out of solution. Two illustrations show the solubility barrier now existing in the art of Reb A and STV sweeteners. For soft drink dispensing equipment designed for an sucrose equivalent (SE—a measure of sweetness) of 12, using a syrup that has an SE of 0.8 would increase the volume of the syrup by a factor of 15 to reach an SE of 12 in a dispensed beverage. Increasing the volume of syrup by a factor of 15 would be uneconomic, and also impractical for small volume goods. In countries that prefer liquid table top non-sucrose (aka "artificial") sweeteners, two drops of liquid sweetener provide the sweetness of a teaspoon of sugar (4 grams). However, two drops (200 µL) of RA97 sweetener (assuming RA97 is 300× sweeter than sucrose) only provides an SE of 0.48 grams of sucrose rather than an SE of 4 grams of sucrose. Known Reb A-based liquid sweeteners have failed commercially because they cannot provide adequate sucrose equivalencies. Ideally, if the solubility problem were overcome, the liquid sweetener could be dried and used as a dry (powdered, agglomerated, or granulated) sweetener.

The sensory profile problem that has impaired commercial acceptance of Reb A and STV sweeteners is typically addressed by using masking agents if lower purity (and more soluble) Reb A or STV is used, or by using higher purity Reb A and STV in much lower volume, as a flavor rather than as a sweetener. Ideally, overcoming the solubility problem would also provide a natural sweetener with an improved sensory profile.

BRIEF SUMMARY OF THE INVENTION

The technical problems to be solved are to provide substantially improved solubility of higher purity Reb A and/or STV, higher sucrose equivalence of liquid Reb A and STV sweeteners, a dried form of such improved RA and STV compositions that retains high solubility when re-dissolved, and improved sensory profiles of such improved RA and STV compositions.

In a particular aspect there is disclosed a composition or a sweetener including one or more steviol glycosides, one or more salts, and one or more natural or synthetic sweeteners. The one or more steviol glycosides can be selected from steviolbioside, stevioside, rebaudioside A, rebaudioside B, rebaudioside C, rebaudioside D, rebaudioside E, rebaudioside F, rubusoside, dulcoside A, and, rebaudioside M. The one or more salts can be selected from any salt that is edible, including but not limited to sodium chloride, potassium chloride, magnesium chloride, sodium sulfate, magnesium sulfate, potassium sulfate, sodium carbonate, potassium carbonate, magnesium carbonate, sodium bicarbonate, and potassium bicarbonate. The one or more natural or synthetic sweeteners are selected from conventional sweeteners such as sucrose, fructose, maltose, lactose, xylitol, sorbitol, dextrose, glucose, mannitol, aspartame, sucralose, acesulfame-K, sodium cyclamate, inulin, erythritol, thaumatin, arabinose, glatactose, mannose, rhamnose, xylose, trehalose, raffinose, cellobiose, tagatose, DOLCIA PRIMA™ allulose, and mogroside, or any other substances that have a sweet taste. In some aspects the composition or sweetener is prepared by hydrolysis of a raw material containing rebaudioside A. The raw material containing rebaudioside A can contain >90 wt. % rebaudioside A, >95 wt. % rebaudioside A, or >99 wt. % rebaudioside A. In other aspects the composition can be prepared by hydrolysis of a raw material containing stevioside. The raw material containing stevioside can contain >90 wt. % stevioside, >95 wt. % stevioside, or >99 wt. % stevioside.

In another aspect the composition or sweetener includes both rebaudioside A and rebaudioside B. The composition or sweetener can include rebaudioside A having 20-100 wt. % of total steviol glycosides in the composition or sweetener. The composition or sweetener can include rebaudioside B having greater than 0 wt. % to 80 wt. % of total steviol glycosides in the composition or sweetener. The composition or sweetener can include rebaudioside B having greater than 0 wt. % to 80 wt. % of the composition or sweetener. The composition or sweetener can include a salt having greater than 0 wt. % to 30 wt. % of the composition or sweetener. The composition or sweetener can include a natural or synthetic sweetener having greater than 0 wt. % to 30 wt. % of the composition or sweetener. The composition or sweetener can also include rebaudioside A and rebaudioside B having about 100% of total steviol glycosides in the composition or sweetener.

In one aspect the composition or sweetener has increased solubility compared to the same composition or sweetener without one or more salt, has increased solubility compared the same composition or sweetener without one or more natural or synthetic sweeteners, and has increased solubility compared the same composition or sweetener without one or more salt and one or more natural or synthetic sweeteners. In another apect the composition or sweetener has improved sensory profile compared to the same composition or sweetener without one or more salt, has improved sensory profile compared to the same composition or sweetener without one or more natural or synthetic sweeteners, and has improved sensory profile compared to the same composition or sweetener without one or more salt and one or more natural or synthetic sweeteners. The composition or sweetener can include Rebaudioside A, Rebaudioside B, glucose, and sodium chloride having about 70 wt. % to about 80 wt. % of Rebaudioside A, 10 wt. % to about 20 wt. % of Rebaudioside B, greater than 0 wt. % to about 5 wt. % of glucose, lactose, galactose, or maltose, and from greater than 0 wt. % to about 5 wt. % of sodium chloride or potassium chloride. In a preferred aspect the Rebaudioside A, Rebaudioside B, glucose, and sodium chloride includes a weight ratio of 77.55: 16.39:3.99:1.30 respectively.

Also disclosed are methods to prepare the composition or sweetener of the embodiments disclosed above.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 1: Tabular data showing the effect of varying the concentration of NaOH in the reaction of RA50, RA80, and RA97 after 18 h at 90° C.

FIG. 5: Tabular data showing a sensory panel for 50% reduced sugar lemon and lime carbonated soda (50% S. R. Lemon & Line CSD) mixed with RA/RB hydrolysate derived from RA97 versus mixed with a commercial RA extract.

FIG. 6: Tabular data showing Anova scores of overall (OV) like, sweetness, bitterness, sugar like, and mouth drying (MD) from the results in FIG. 5.

FIG. 7: Tabular data showing the average overall (OV) like, sweetness, bitterness, sugar like, and mouth drying (MD) from the results in FIG. 5.

DETAILED DESCRIPTION

Figure 2:
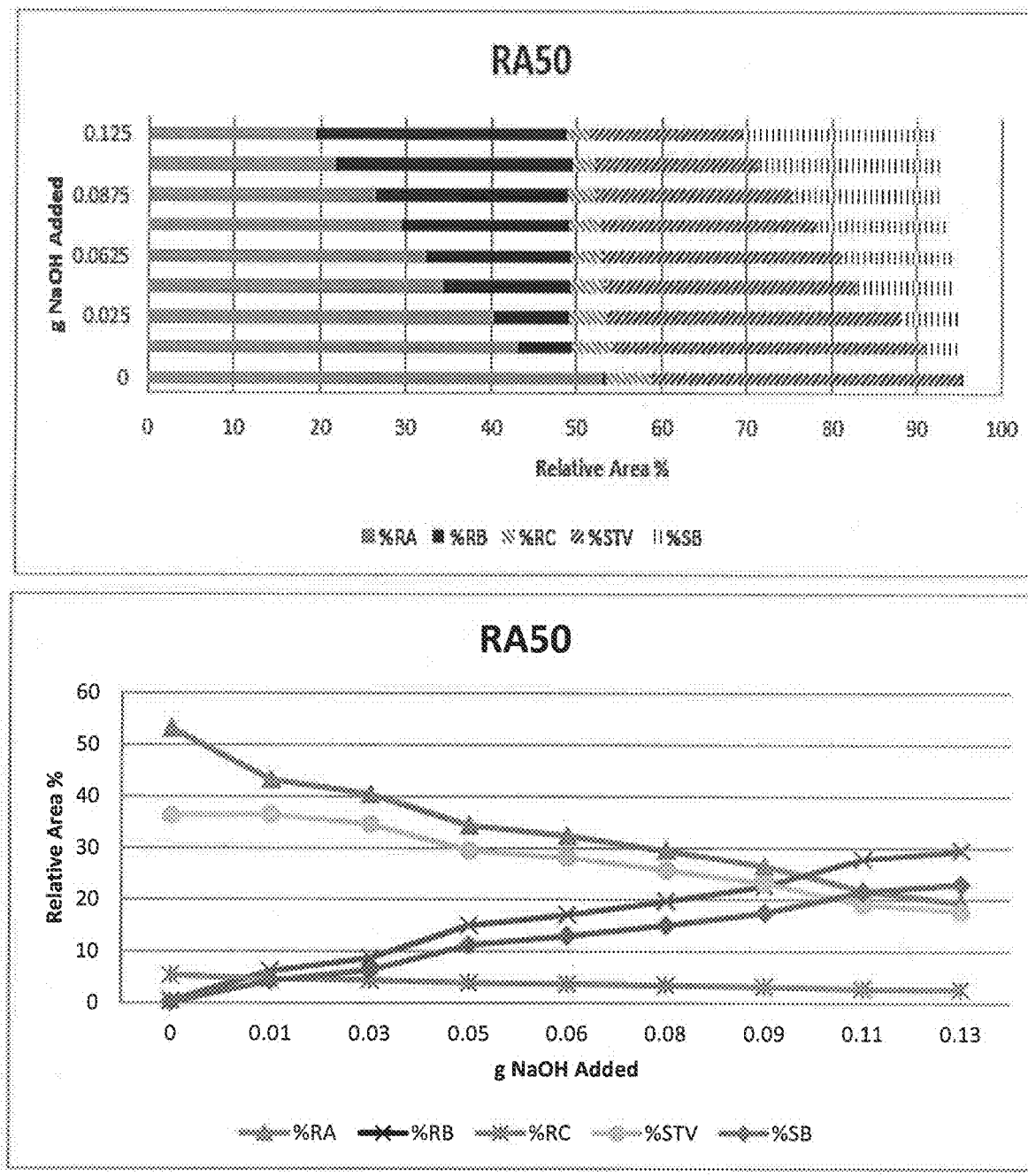
FIG. 2: Graphical illustrations showing the effect of varying the concentration of NaOH in the reaction of RA50 after 18 h at 90° C.
Figure 3:
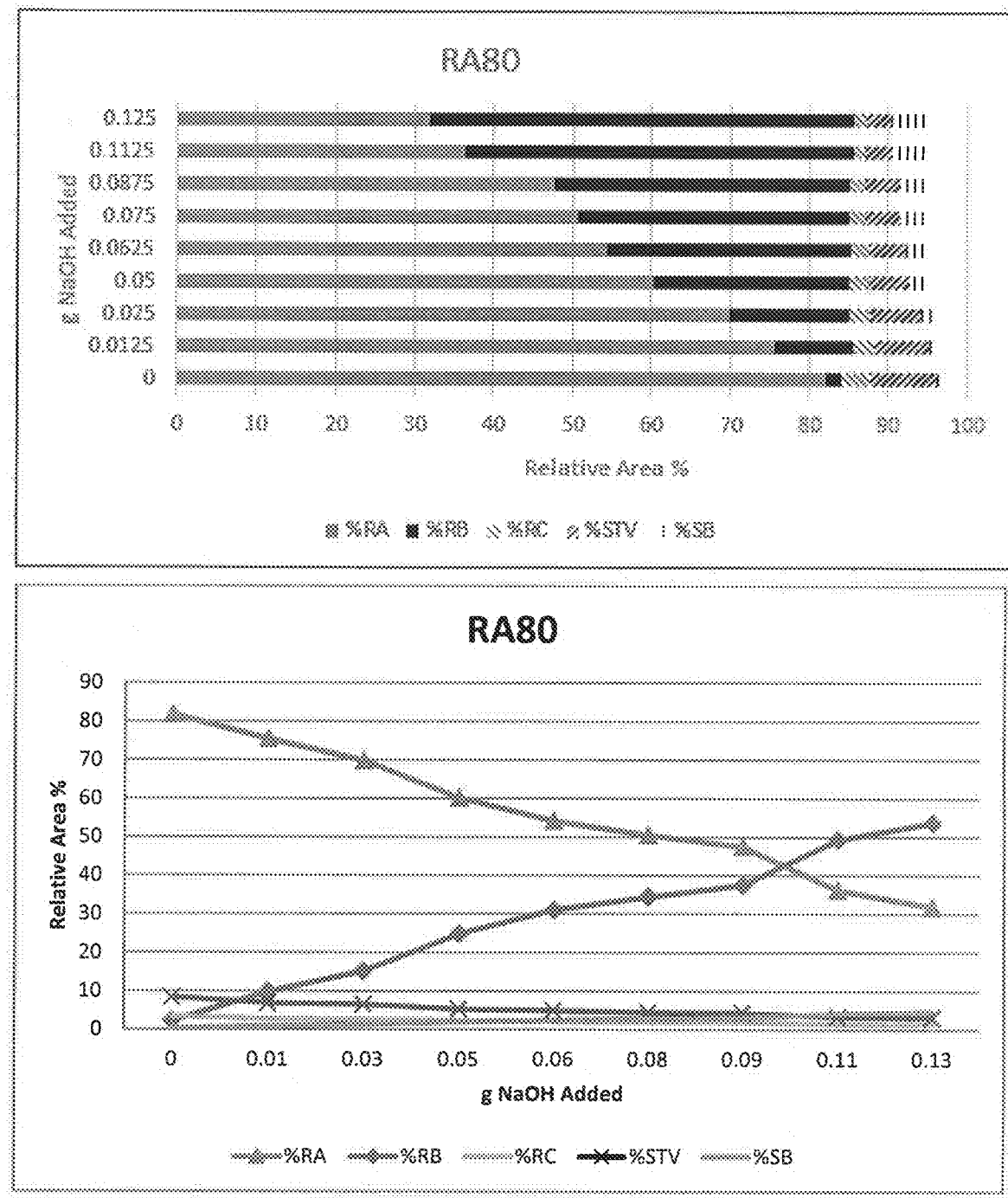
FIG. 3: Graphical illustrations showing the effect of varying the concentration of NaOH in the reaction of RA80 after 18 h at 90° C.
Figure 4:
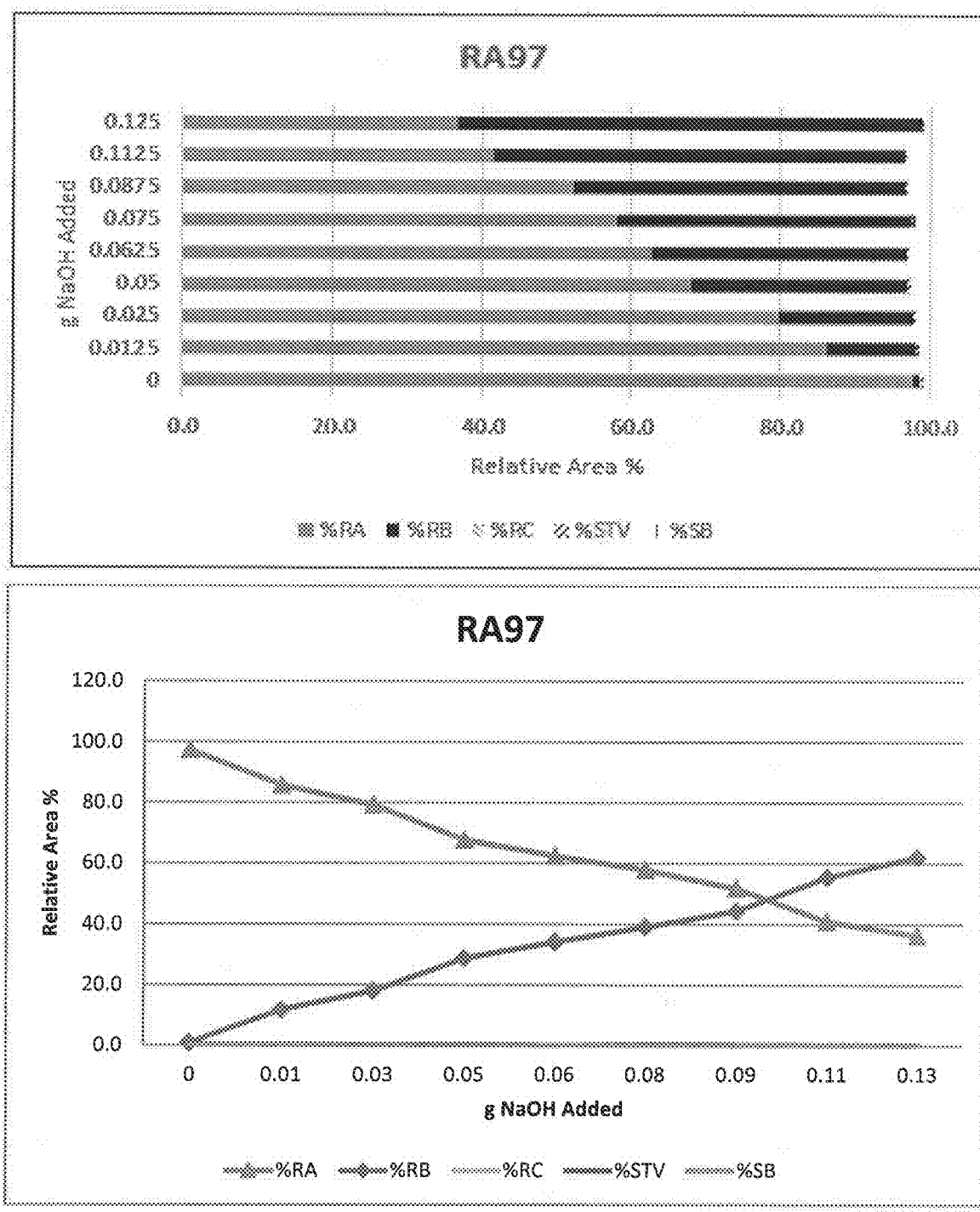
FIG. 4: Graphical illustrations showing the effect of varying the concentration of NaOH in the reaction of RA97 after 18 h at 90° C.
Figure 8:
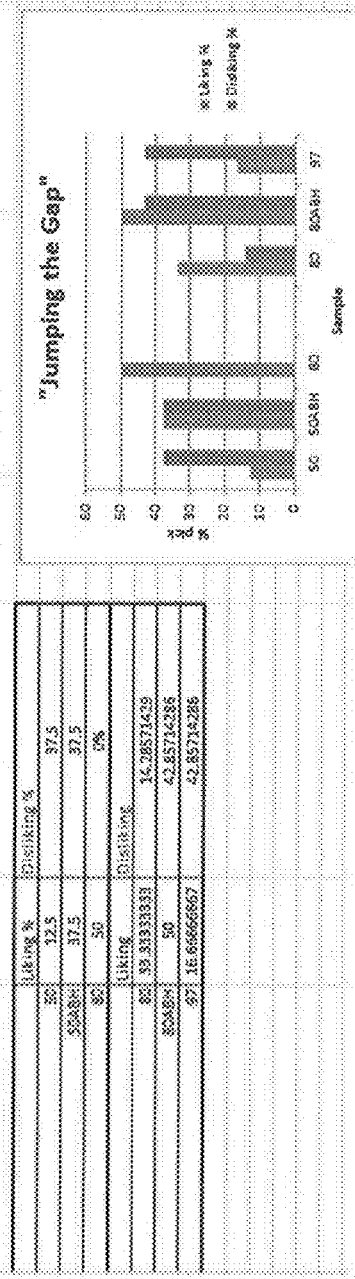
FIG. 8: Tabular data and graphical illustrations showing the sensory panel results for RA (RA50, RA80, and RA97) and RA/RB hydrolysates (ABH) compositions.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The phrase "*Stevia* starting material" or "raw material" means a material containing steviol glycosides of the plant *Stevia rebaudiana* or other species of *Stevia* genus. The *Stevia* starting material or raw material can be a crude extract, a purified extract, or a byproduct of a purification process. A crude extract is typically the first dried product produced after processing harvested *Stevia* plant material. A purified extract contains a higher concentration of one or more steviol glycosides of interest than contained in a crude extract. A byproduct of a purification process typically is all or a portion of the waste stream from purifying steviol glycosides from crude extract or from an intermediate purity.

The acronym "RAxx" is used herein to denote a purity of Rebaudioside A final product isolated from crude extract of *Stevia*, where "xx" is a number between 01 and 99 and is the percentage of Rebaudioside A in the dried product. More generally, acronyms of the type "YYxx" are used herein to denote the purity of a given ingredient denoted by the placeholder "YY", as a mass percentage of a compound, where "xx" is a number between 01 and 99 and is the percentage of product YY in the product. For instance, a compound that is 95% steviol glycosides ("SG") would be denoted "SG95", and a compound that is 97% stevioside ("STV") would be denoted "STV97". A product of that is 97% Rebaudioside A would be denoted "RA97". Denoted percentages include a range of approximately 0.5% above and below a whole number percentage, unless otherwise indicated. For instance, "99% or higher purity Reb A" would include purity between 98.5% Reb A and RA100, whereas "RA97" would include a range of 96.5% to 97.5%. "RA99+" means greater than 99.0% purity Reb A. "Pure Reb A" is denoted as RA100, and is defined in U.S. Patent Application Publication No. 2006/0083838.

The phrase "steviol glycosides" is recognized in the art and is intended to include the major and minor constituents of *Stevia*. These include, but are not limited to components of *Stevia* such as Steviol, Steviolbioside, Stevioside, Rebaudioside A (RA), Rebaudioside B (RB), Rebaudioside C (RC), Rebaudioside D (RD), Rebaudioside E (RE), Rebaudioside F (RF), Rubusoside and Dulcoside A (DA).

The phrase "*Stevia* containing sweetener" is intended to include any composition that is prepared from a *Stevia* plant, such as a *Stevia* extract, or the individual components found in *Stevia*. The sweetener can include one or more of the components associated with the *Stevia* plant, such as those noted above.

A "*Stevia* composition" as referred to herein, pertains to a material that includes one or more steviol glycosides found in the *Stevia* plant.

The phrase "sucrose equivalence" is the amount of non-sucrose sweetener required to provide the sweetness of a given percentage of sucrose in the same food, beverage, or solution. For instance, a non-diet soft drink typically contains 12 grams of sucrose per 100 ml of water, i.e., 12% sucrose. This means that to be commercially accepted diet soft drinks must have the same sweetness as a 12% sucrose soft drink, i.e., a diet soft drink must have 12% sucrose equivalence ("SE"). Soft drink dispensing equipment assumes an SE of 12%, since such equipment is set up for use with sucrose-based syrups.

The phase "sensory profile" is defined as the temporal profile of all basic tastes of a sweetener. The onset and decay of sweetness when a sweetener is consumed, as perceived by trained human tasters and measured in seconds from first contact with a taster's tongue ("onset") to a cutoff point (typically 180 seconds after onset), is called the "temporal profile of sweetness". A plurality of such human tasters is called a "sensory panel". In addition to sweetness, sensory panels can also judge the temporal profile of the other "basic tastes": bitterness, saltiness, sourness, piquance (aka spiciness), and umami (aka savoriness or meatiness). The onset and decay of bitterness when a sweetener is consumed, as perceived by trained human tasters and measured in seconds from first perceived taste to the last perceived aftertaste at the cutoff point, is called the "temporal profile of bitterness".

The term "flavor" or "flavor characteristic", as used herein, is the combined sensory perception of the components of taste, odor, and/or texture. The term "enhance", as used herein, includes augmenting, intensifying, accentuating, magnifying, and potentiating the sensory perception of a flavor characteristic without changing the nature or quality thereof. The term "modify", as used herein, includes altering, varying, suppressing, depressing, fortifying and supplementing the sensory perception of a flavor characteristic where the quality or duration of such characteristic was deficient.

The technical problems are solved by the invention disclosed and claimed herein.

While not to be bound by theory, the inventors have discovered the unexpected result when one or more steviol glycosides, whether prepared by hydrolysis or not, are combined with one or more salts and one or more natural or synthetic sweeteners have improved solubility and sensory profiles.

By combining steviol glycosides, including all possible combinations of the steviol glycosides disclosed herein, with one or more salts and one or more natural or synthetic sweeteners in a composition results in improved solubility and sensory profile as described and can be used as a sole sweetener of food, beverage, medicine, tobacco, pharmaceutical, and personal care products.

The one or more steviol glycosides can include steviolbioside, stevioside, rebaudioside A, rebaudioside B, rebaudioside C, rebaudioside D, rebaudioside E, rebaudioside F, rubusoside, dulcoside A, and rebaudioside M.

The one or more steviol glycosides contained in the sweetening composition can make up anywhere from about 20 wt. % of the sweetening composition to about 99 wt. % of the sweetening composition, specifically about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, about 85 wt. %, about 86 wt. %, about 87 wt. %, about 88 wt. %, about 89 wt. %, about 90 wt. %, about 91 wt. %, about 92 wt. %, about 93 wt. %, about 94 wt. %, about 95 wt. %, about 96 wt. %, about 97 wt. %, about 98 wt. %, about 99 wt. %, and all ranges therebetween, including for example from about 40 wt. % to about 70 wt.

%, from about 50 wt. % to about 80 wt. %, from about 60 wt. % to about 90 wt. %, or from about 80 wt. % to about 99 wt. %.

The sweetening composition can include one or more natural or synthetic sweeteners. Such sweeteners include conventional sweeteners (cane sugar, beet sugar, honey, syrups, sucrose, fructose, maltose, xylitol, sorbitol, dextrose, glucose, mannitol, arabinose, glatactose, mannose, rhamnose, xylose, and other "natural" sweeteners) and artificial or synthetic sweeteners (cyclamates and salts thereof, saccharin and salts thereof, sucralose, aspartame, a *Stevia* composition, acesulfame-K, neotame, thaumatin, erythritol, trehalose, raffinose, cellobiose, tagatose, DOLCIA PRIMA™ allulose, inulin, N—[N43-(3-hydroxy-4-methoxyphenyl)propyl]-alpha-aspartylR-phenylalanine 1-methyl ester (hereinafter abbreviated as "ANS9801"), glycyrrhizin, thaumatin, monellin and other chemically produced high-intensity sweeteners). Alternatively, the one or more natural or synthetic sweeteners can be any substance that has a sweet taste.

The one or more natural or synthetic sweeteners in addition to the steviol glycosides of the sweetening composition can make up anywhere from about 0.1 wt. % of the sweetening composition to about 50 wt. % of the sweetening composition, specifically about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, and all ranges therebetween, including for example from about 1 wt. % to about 20 wt. %, from about 10 wt. % to about 30 wt. %, from about 20 wt. % to about 40 wt. %, or from about 30 wt. % to about 50 wt. %.

The sweetening composition of the current embodiments can include one or more salts. The one or more salt can include sodium carbonate, sodium bicarbonate, sodium chloride, potassium chloride, magnesium chloride, sodium sulfate, magnesium sulfate, and potassium sulfate, or any edible salt, for example a metal or metal alkali halide, a metal or metal alkali carbonates, bicarbonates, a metal or metal alkali phosphates, biphosphates, pyrophospate, triphosphate, metaphosphate, a metal or metal alkali sulfate or metabisulfate.

The one or more salts can make up anywhere from about 0.1 wt. % of the sweetening composition to about 50 wt. % of the sweetening composition, specifically about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, and all ranges therebetween, including for example from about 0.1 wt. % to about 2 wt. %, from about 5 wt. % to about 20 wt. %, or from about 10 wt. % to about 30 wt. %.

Alternatively while not to be limited by theory, the sweetening composition containing steviol glycosides of the current embodiments can include only a trace amount or may exclude either a salt or a natural or synthetic sweetener if the solubility and/or the sensory profile are satisfactory for a given use or purpose of the sweetening composition. In one embodiment, greater than 0 wt. % represents a trace amount of material in the composition as well as percentages noted above, such as 0.1 wt. %, etc.

All of the components of the sweetening composition can be purchased or be made by processes known to those of ordinary skill in the art and combined (e.g., precipitation/co-precipitation, mixing, blending, grounding, mortar and pestal, microemulsion, solvothermal, sonochemical, etc.).

In one aspect, Rebaudioside A can be hydrolyzed to lyse a glucose unit from the glycoside chain on the C13 carbon of Reb A, which converts Reb A to Reb B. Stevioside can be hydrolyzed to lyse a glucose unit from the glycoside chain on the C13 carbon of stevioside, which converts STV to STB. The inventors discovered the unexpected result that the solubility and sensory profile of the products of hydrolysis (RA and RB, and STV and STB) is improved compared to plain mixtures of RA and RB, and STV and STB, made from purified RA and RB, and purified STV and STB, starting materials. While not to bond by theory, the inventors believe that the results are due to the glucose and salts generated in the hydrolysis process, i.e. the hydrolysate is a composition comprising additional components, in addition to RA and RB, and thus is different from the plain mixture. In other words, if the same molar concentration of purified Reb A and Reb B are mixed and dissolved, the Reb A and Reb B rapidly precipitate out of solution. The hydrolyzed RA/RB, and hydrolyzed STV/STB, stays in solution. For clarification purposes, "RA/RB" means the products of alkaline hydrolysis of Reb A and "STV/STB" means the products of alkaline hydrolysis of STV.

In one aspect Rebaudioside A can be hydrolyzed to lyse a glucose unit from the glycoside chain on the C13 carbon of Reb A, which converts Reb A to Reb B, and thus the mole ratio of rebaudioside B and glucose is about 1:1.

Alkaline hydrolysis of the starting or raw material is preferred for simplicity and economics. Enzymatic lysis of a glucose unit from the C13 carbon of Reb A or STV can also be used. Sodium hydroxide is the preferred alkali to use for hydrolysis of Reb A and STV, but potassium hydroxide and other well-known alkali used in food processing can be used.

The starting or raw materials can include >50 wt. % of rebaudioside A or stevioside, >55 wt. % of rebaudioside A or stevioside, >60 wt. % of rebaudioside A or stevioside, >65 wt. % of rebaudioside A or stevioside, >70 wt. % of rebaudioside A or stevioside, >75 wt. % of rebaudioside A or stevioside, >80 wt. % of rebaudioside A or stevioside, >85 wt. % of rebaudioside A or stevioside, >90 wt. % of rebaudioside A or stevioside, >95 wt. % of rebaudioside A or stevioside, or >99 wt. % of rebaudioside A or stevioside.

Reb A starting material is dissolved in water (preferably potable water), alkali added, and the solution temperature raised preferably to 85° C. to 95° C., and more preferably to 90° C. If the alkaline hydrolysis is conducted at temperatures lower than 85° C., the reaction proceeds slowly until the alkali is exhausted. The solution is stirred and is maintained at the selected temperature for a duration that provides the desired concentrations of RA and RB in the solution or until the alkali is exhausted. The preferred duration of alkaline hydrolysis at commercial scale is a minimum 30 minutes; shorter durations typically do not exhaust the amounts of alkali used in commercial production. The final RA/RB solution is typically very close to pH 7.0, but pH can be adjusted (typically by adding HCl or NaOH).

The process described above used to produce an RA/RB solution also hydrolyzes any STV present in the *Stevia* starting material to an STV/STB solution.

The RA/RB (and STV/STB) solution produced as described above is brown in color, has a faint "burnt sugar" smell, and has a weak "caramel" taste. The brown color, burnt sugar smell, and caramel taste can be removed by column chromatography such as an activated charcoal column, a polymer resin adsorption column or with an ion exchange column as the chromatography matrix, binding the caramel components to the column while letting the steviol glycosides pass through. Depending upon the beverage, food, or other comestible in which the RA/RB (or STV/STB) is used, the brown color, burnt sugar smell, and caramel taste may be desirable, or unnoticeable, in either case avoiding the need to remove the brown color, burnt sugar smell, and caramel taste.

The inventors' experimental results, including a hydrolysis studies and a sensory profile studies are disclosed herein and reported throughout the Figures following the specification. Many variations of alkaline molarity, Reb A purity, STV purity, and reaction time were tested, as disclosed. Reverse osmosis water was used as the solvent in all of the experiments. Solubility of RA/RB and STV/STB products are a function of alkaline concentration in the hydrolysis step.

The RA/RB, and STV/STB, products can be kept in solution as a syrup ready for distribution as a liquid sweetener, or dried for distribution as a dry sweetener. Drying is by spray-drying, lyophilization, oven drying, and other drying processes well-known in the art of sweeteners.

To modify the perceived sweetness of orally consumable compositions containing the Product, The Product can be modified by the addition of taste modifying moieties, such as galactosides. For instance, β-1,4-galactosyl can be substituted on the Product using a β-1,4-galactosyl transferase enzyme in reactions known in the art. Such Product modified by one or more functional groups is included in the term "Product".

The term "iso-sweet" as used herein is intended to mean that the subject composition has a sweetness equal to that of sugar.

For use as a co-sweetener, the Product can be used in ways known in the art of sweeteners (e.g., steam, ethanol, or alkanol aerosolized Product vapor-deposited on a co-sweetener) to coat or permeate other solid sweeteners, such granular and powdered sugar and artificial sweeteners, to be mixed as a separate powder with such solid sweeteners, to be co-crystallized with other solid sweeteners, or to be suspended or dissolved in liquid sweeteners, such as corn syrup and honey. Commercially available spray dryers used in the ethanol purge and drying stage of the industrial embodiment can typically be configured to produce a particulate size of Product appropriate for an intended use.

In the art of flavoring foodstuffs and medicinal compositions, there is a continuing need for compositions which can modify and improve the flavor of such materials, because acceptance and demand for foodstuffs and medicinal products is generally related to the sensory perception of them. In the art of flavoring oral hygiene compositions, such as mouthwash and toothpaste, and in the art of flavoring chewing compositions, such as chewing tobacco, snuffs and chewing gum, there is a need to improve the flavor characteristics of such chewing compositions with flavor modifiers or enhancers which are non-cariogenic and do not support the growth of tooth decay producing streptococci, lactobacilli, or the like. Likewise, there is need to improve the flavor characteristics of smoking compositions.

The term "orally consumable composition" includes foodstuffs, medicinal compositions, smoking compositions, chewing compositions and oral hygiene compositions, including mouthwashes and toothpastes. The term "foodstuff" includes both solid and liquid ingestible materials which usually do, but need not, have a nutritional value and are intended for consumption by man or animal. Representative examples of foodstuff include coffee, teas, herbal teas, baked goods, natural and synthetic flavors, spices, condiments, soups, stews, convenience foods, beverages (both carbonated and non-carbonated), dairy products, candies, vegetables, cereals, fruits, fruit drinks, snacks, cocoa products, chocolates, animal feed, and the like. The term "medicinal composition" includes solids, gases and liquids which are ingestible materials having medicinal value, such as cough syrups, cough drops, medicinal sprays, vitamins, and chewable medicinal tablets. The term "chewing compositions" include chewing tobacco, smokeless tobacco, snuff, chewing gum and other compositions which are masticated and subsequently expectorated. Chewing gum includes compositions which comprise a substantially water-insoluble, chewable gum base, such as chicle or substitutes therefor, including jetulong, guttakay rubber or certain comestible natural synthetic resins or waxes. The term "oral hygiene compositions" includes mouthwashes, mouth rinses, toothpastes, tooth polishes, dentifrices, mouth sprays, and mouth refreshers. The term "smoking composition", as used herein, includes cigarette, pipe and cigar tobacco, and all forms of tobacco such as shredded filler, leaf, stem, stalk, homogenized leaf cured, reconstituted binders, and reconstituted tobacco from tobacco dust, fines, or other sources in sheet, pellet or other forms. "Smoking compositions" also include tobacco substitutes formulated from non-tobacco materials, such as representative tobacco substitutes described in U.S. Pat. Nos. 3,529,602, 3,703,177 and 4,079,742 and references cited therein.

In accordance with one embodiment of this invention, an orally consumable composition having flavor enhanced or modified by the Product is provided. The Product can modify or enhance flavor characteristics that are sweet, fruity, floral, herbaceous, spicy, aromatic, pungent, "nut-like" (e.g., almond, pecan), "spicy" (e.g., cinnamon, clove, nutmeg, anise and wintergreen), "non-citrus fruit" flavor (e.g., strawberry, cherry, apple, grape, currant, tomato, gooseberry and blackberry), "citrus fruit" flavor (e.g., orange, lemon and grapefruit), and other useful flavors, including coffee, cocoa, peppermint, spearmint, vanilla and maple.

In accordance with one variation of this embodiment, an orally consumable composition comprises a Product in an amount effective to sweeten or to modify or enhance the taste, odor and/or texture of the orally consumable composition.

The terminology "amount effective" or "effective amount" means an amount that produces a sensory perception. The use of an excessive amount of a Product will produce sweetness that may not be desired for flavor modification or enhancement, just as too much sugar can be added to a foodstuff or beverage. The amount of Product employed can vary over a relatively wide range, depending upon the desired sensory effect to be achieved with the orally consumable composition and the nature of the initial composition.

The Product can be added to an orally consumable composition by admixing the Product with the orally consumable composition or admixing the Product with a component of the orally consumable composition.

The Product can be used in tobacco and tobacco-related products selected from the group comprising cigarettes, cigars, snuffs, chewing tobacco, other tobacco goods, filters, smoking papers, and other smoking compositions. A smoking composition having a sweetened, enhanced, or modified flavor comprises a smoking filler material selected from the group consisting of tobacco, reconstituted tobacco, non-tobacco substitutes and mixtures thereof, and containing an effective amount of Product. "Containing" means both being included as an ingredient and being adsorbed to a material. In one variation of this embodiment, the smoking composition comprises a filter means containing a Product. The term "filter means", as used herein, includes a smoking device means such as a cigar or cigarette holder having a filtering or flavoring module incorporated therein and includes acetate, cotton, charcoal and other fiber, flake or particle filtering means. In another variation of this embodiment, the smoking composition comprises a wrapper means containing a Product. In one variation of this embodiment of this invention, 0.003 to 0.30 parts by weight of a Product is added to 100 parts by weight of the smoking filler material. In a preferred variation of this embodiment of this invention, 0.015 to 0.30 parts by weight of a Product is added to 100 parts of a weight of a smoking filler material.

Those skilled in the art of flavoring tobacco understand that the effective amount of the Product added to a smoking composition may depend upon the method in which the Product is added to the smoking composition and to which portion of the smoking composition Product is added. Product can be added directly to the smoking filler material, to the filter means, or to the wrapper means of a smoking composition. Product can be added to a filter means of a smoking composition by any manner known to those skilled in the art of flavoring filter means, including but not limited to, incorporating the Product among the fibers, flakes or particles of a filter means, filling the Product between two or more layers of fibers of a fiber filter means to form a triple filter means, or inserting the Product into a smoking device means, such as a cigarette holder.

It is apparent to those skilled in the art that only a portion of the smoking filler material or filter means need be treated with a Product, since blending or other operations may be used to adjust the final or ultimate smoking composition within the effective or desired ranges of concentration of Product. In addition to Product, other flavorings or aroma additives known in the smoking composition flavoring art may be used with Product and added along with Product to the smoking composition. Representative flavorings used in the smoking composition flavoring art include ethyl acetate, isoamyl acetate, propyl isobutyrate, isobutyl butyrate, ethyl butyrate, ethyl valerate, benzyl formate, menthol, limonene, cymene, pinene, linalool, geraniol, citroneilol, citral, peppermint oil, orange oil, coriander oil, lemon oil, borneol, cocoa extract, tobacco extract, licorice extract and fruit extractives.

The Product, in its purified state after spray drying, is generally a fine powder, having a particle size in the range of about 1 to 100 microns. Fine powders are difficult to handle and difficult to admix with orally consumable compositions, such as tea leaves, tobacco products, herb leaves, coffees and other orally consumable compositions. Also, generally, only a relatively small amount of Product is used with an orally consumable composition when the Product is used as a flavor modifier or enhancer, sweetener, or co-sweetener.

In accordance with another embodiment of this invention, a process for adding Product to an orally consumable composition comprises admixing Product with a carrier to form a Product-carrier mixture. Preferred carriers include water, ethanol, other alkanols used in food processing, or mixtures thereof. The Product solution so formed is contacted with an orally consumable composition, and the carrier is removed from the orally consumable composition by evaporation, or otherwise, and the Product residues deposited with the orally consumable composition. This process is particularly useful for adding Product to tea leaves, herbal plant leaves, and other sweeteners, particularly granular sucrose (table sugar).

In accordance with still another embodiment of this invention, a liquid filter material, suitable for use with an orally consumable composition, is prepared with Product. The term "liquid filter", as used herein, refers to a porous or semi-porous filter material used for preparation of an orally consumable composition such as a tea bag, a coffee filter or a filter disk. The term "filter disk" refers to a porous or semi-porous inactive article added to an orally consumable composition for the purposes of acting as a vehicle for the addition of a flavoring or sweetening composition to the orally consumable composition. A process for preparing a liquid filter comprising a filter material and Product is typically by admixing Product with a carrier to form a Product-carrier mixture; contacting the Product-carrier mixture with the filter material; and removing the carrier from the filter material thereby depositing a Product residue on the filter material.

The Product can be used in beverages, broths, and beverage preparations selected from the group comprising carbonated, non-carbonated, frozen, semi-frozen ("slush"), non-frozen, ready-to-drink, concentrated (powdered, frozen, or syrup), dairy, non-dairy, herbal, non-herbal, caffeinated, non-caffeinated, alcoholic, non-alcoholic, flavored, non-flavored, vegetable-based, fruit-based, root/tuber/corm-based, nut-based, other plant-based, cola-based, chocolate-based, meat-based, seafood-based, other animal-based, algae-based, calorie enhanced, calorie-reduced, and calorie-free products, optionally dispensed in open containers, cans, bottles or other packaging. Such beverages and beverage preparations can be in ready-to-drink, ready-to-cook, ready-to-mix, raw, or ingredient form and can use the Product as a sole sweetener or as a co-sweetener.

The Product can be used in foods and food preparations (e.g., sweeteners, soups, sauces, flavorings, spices, oils, fats, and condiments) selected from the group comprising dairy-based, cereal-based, baked, vegetable-based, fruit-based, root/tuber/corm-based, nut-based, other plant-based, egg-based, meat-based, seafood-based, other animal-based, algae-based, processed (e.g., spreads), preserved (e.g., meals-ready-to-eat rations), and synthesized (e.g., gels) products. Such foods and food preparations can be in ready-to-eat, ready-to-cook, ready-to-mix, raw, or ingredient form and can use the Product as a sole sweetener or as a co-sweetener.

The Product can be used in candies, confections, desserts, and snacks selected from the group comprising dairy-based, cereal-based, baked, vegetable-based, fruit-based, root/tuber/corm-based, nut-based, gum-based, other plant-based, egg-based, meat-based, seafood-based, other animal-based, algae-based, processed (e.g., spreads), preserved (e.g., meals-ready-to-eat rations), and synthesized (e.g., gels) products. Such candies, confections, desserts, and snacks can be in ready-to-eat, ready-to-cook, ready-to-mix, raw, or ingredient form, and can use the Product as a sole sweetener or as a co-sweetener.

The Product can be used in prescription and over-the-counter pharmaceuticals, assays, diagnostic kits, and therapies selected from the group comprising weight control, nutritional supplement, vitamins, infant diet, diabetic diet, athlete diet, geriatric diet, low carbohydrate diet, low fat diet, low protein diet, high carbohydrate diet, high fat diet, high protein diet, low calorie diet, non-caloric diet, oral hygiene products (e.g., toothpaste, mouthwash, rinses, floss, toothbrushes, other implements), personal care products (e.g., soaps, shampoos, rinses, lotions, balms, salves, ointments, paper goods, perfumes, lipstick, other cosmetics), professional dentistry products in which taste or smell is a factor (e.g., liquids, chewables, inhalables, injectables, salves, resins, rinses, pads, floss, implements), medical, veterinarian, and surgical products in which taste or smell is a factor (e.g., liquids, chewables, inhalables, injectables, salves, resins, rinses, pads, floss, implements), and pharmaceutical compounding fillers, syrups, capsules, gels, and coating products.

The Product can be used in consumer goods packaging materials and containers selected from the group comprising plastic film, thermoset and thermoplastic resin, gum, foil, paper, bottle, box, ink, paint, adhesive, and packaging coating products.

The Product can be used in goods selected from the group comprising sweeteners, co-sweeteners, coated sweetener sticks, frozen confection sticks, medicine spoons (human and veterinary uses), dental instruments, pre-sweetened disposable tableware and utensils, sachets, edible sachets, pot pourris, edible pot pourris, hotch potches, edible hotch potches, artificial flowers, edible artificial flowers, clothing, edible clothing, massage oils, and edible massage oils.

The following paragraphs enumerated consecutively from 1 through 57 provide for various aspects of the present invention. In one embodiment, in a first paragraph (1), the present invention provides a sweetening composition comprising one or more steviol glycosides, one or more salts, and one or more natural or synthetic sweeteners.

2. The composition according to paragraph 1, wherein the one or more steviol glycosides are selected from steviolbioside, stevioside, rebaudioside A, rebaudioside B, rebaudioside C, rebaudioside D, rebaudioside E, rebaudioside F, rubusoside, dulcoside A, and, rebaudioside M.

3. The composition according to any of paragraphs 1 to 2, wherein the one or more salts are selected from sodium chloride, potassium chloride, magnesium chloride, sodium sulfate, magnesium sulfate, potassium sulfate, sodium carbonate, potassium carbonate, magnesium carbonate, sodium bicarbonate, and potassium bicarbonate.

4. The composition according to any of paragraphs 1 to 3, wherein the one or more natural or synthetic sweeteners are selected from sucrose, fructose, maltose, xylitol, sorbitol, dextrose, glucose, mannitol, aspartame, sucralose, acesulfame-K, sodium cyclamate, inulin, erythritol, thaumatin, arabinose, glatactose, mannose, rhamnose, xylose, trehalose, raffinose, cellobiose, tagatose, DOLCIA PRIMA™ allulose, and mogroside.

5. The composition according to any of paragraphs 1 to 4, wherein the composition is prepared by hydrolysis of a raw material comprising rebaudioside A.

6. The composition according to any of paragraphs 1 to 5, wherein the raw material comprises >90 wt. % rebaudioside A.

7. The composition according to any of paragraphs 1 to 6, wherein the raw material comprises >95 wt. % rebaudioside A.

8. The composition according to any of paragraphs 1 to 7, wherein the raw material comprises >99 wt. % rebaudioside A.

9. The composition according to any of paragraphs 1 to 8, wherein the composition is prepared by hydrolysis of a raw material comprising stevioside.

10. The composition according to any of paragraphs 1 to 9, wherein the raw material comprises >90 wt. % stevioside.

11. The composition according to any of paragraphs 1 to 10, wherein the raw material comprises >95 wt. % stevioside.

12. The composition according to any of paragraphs 1 to 11, wherein the raw material comprises >99 wt. % stevioside.

13. The composition according to any of paragraphs 1 to 12, wherein the composition comprises both rebaudioside A and rebaudioside B.

14. The composition according to any of paragraphs 1 to 13, wherein rebaudioside A comprises 20-100 wt. % of total steviol glycosides in the composition.

15. The composition according to any of paragraphs 1 to 14, wherein rebaudioside B comprises 0-80 wt. % of total steviol glycosides in the composition.

16. The composition according to any of paragraphs 1 to 15, wherein rebaudioside A comprises 20-100 wt. % of the composition.

17. The composition according to any of paragraphs 1 to 16, wherein rebaudioside B comprises 0-80 wt. % of the composition.

18. The composition according to any of paragraphs 1 to 17, wherein salt comprises 0-30 wt. % of the composition.

19. The composition according to any of paragraphs 1 to 18, wherein natural or synthetic sweetener comprises 0-30 wt. % of the composition.

20. The composition according to any of paragraphs 1 to 19, wherein the rebaudioside A and rebaudioside B comprises about 100% of total steviol glycosides in the composition.

21. The composition according to any of paragraphs 1 to 20, where the composition has increased solubility compared to the same composition without one or more salt.

22. The composition according to any of paragraphs 1 to 21, where the composition has increased solubility compared to the same composition without one or more natural or synthetic sweeteners.

23. The composition according to any of paragraphs 1 to 22, where the composition has increased solubility compared to the same composition without one or more salt and one or more natural or synthetic sweeteners.

24. The composition according to any of paragraphs 1 to 23, where the composition has improved sensory profile compared to the same composition without one or more salt.

25. The composition according to any of paragraphs 1 to 24, where the composition has improved sensory profile compared to the same composition without one or more natural or synthetic sweeteners.

26. The composition according to any of paragraphs 1 to 25, where the composition has improved sensory profile compared to the same composition without one or more salt and one or more natural or synthetic sweeteners.

27. The composition according to any of paragraphs 1 to 26, comprising Rebaudioside A, Rebaudioside B, glucose, and sodium chloride.

28. The composition according to any of paragraphs 1 to 27, comprising from about 70 wt. % to about 80 wt. % of Rebaudioside A.

29. The composition according to any of paragraphs 1 to 28, comprising from about 10 wt. % to about 20 wt. % of Rebaudioside B.

30. The composition according to any of paragraphs 1 to 29, comprising from about 1 wt. % to about 5 wt. % of glucose, lactose, galactose, or maltose.

31. The composition according to any of paragraphs 1 to 30, comprising from about 1 wt. % to about 5 wt. % of sodium chloride or potassium chloride.

32. The composition according to any of paragraphs 1 to 31, comprising Rebaudioside A, Rebaudioside B, glucose, and sodium chloride in a weight ratio of 77.55:16.39:3.99: 1.30 respectively.

33. The composition according to any of paragraphs 1 to 32, comprising Rebaudioside A, Rebaudioside B, glucose, and sodium chloride.

34. A sweetener, comprising one or more steviol glycosides, one or more salts, and one or more natural or synthetic sweeteners.

35. The sweetener according to paragraph 34, wherein the one or more steviol glycosides are selected from steviolbioside, stevioside, rebaudioside A, rebaudioside B, rebaudioside C, rebaudioside D, rebaudioside E, rebaudioside F, rubusoside, dulcoside A, and rebaudioside M.

36. The sweetener according to any of paragraphs 34 to 35, wherein the one or more salts are selected from sodium chloride, potassium chloride, magnesium chloride, sodium sulfate, magnesium sulfate, potassium sulfate, sodium carbonate, potassium carbonate, magnesium carbonate, sodium bicarbonate, and potassium bicarbonate.

37. The sweetener according to any of paragraphs 34 to 36, wherein the one or more natural or synthetic sweeteners are selected from sucrose, fructose, maltose, xylitol, sorbitol, dextrose, glucose, mannitol, aspartame, inulin, sucralose, acesulfame-K, sodium cyclamate, erythritol, thaumatin, arabinose, glatactose, mannose, rhamnose, xylose, trehalose, raffinose, cellobiose, tagatose, DOLCIA PRIMA™ allulose, and mogroside.

38. The sweetener according to any of paragraphs 34 to 37, where the composition has increased solubility compared to the same sweetener without one or more salt.

39. The sweetener according any of paragraphs 34 to 38, where the composition has increased solubility compared to the same sweetener without one or more natural or synthetic sweeteners.

40. The sweetener according to any of paragraphs 34 to 39, where the composition has increased solubility compared to the same sweetener without one or more salt and one or more natural or synthetic sweeteners.

41. The sweetener according to any of paragraphs 34 to 40, where the composition has an improved sensory profile compared to the same sweetener without one or more salt.

42. The sweetener according to any of paragraphs 34 to 41, where the composition has an improved sensory profile compared to the same sweetener without one or more natural or synthetic sweeteners.

43. The sweetener according to any of paragraphs 34 to 42, where the composition has an improved sensory profile compared to the same sweetener without one or more salt and one or more natural or synthetic sweeteners.

44. The sweetener according to any of paragraphs 34 to 43, comprising from about 70 wt. % to about 80 wt. % of Rebaudioside A.

45. The sweetener according to any of paragraphs 34 to 44, comprising from about 10 wt. % to about 20 wt. % of Rebaudioside B.

46. The sweetener according to any of paragraphs 34 to 45, comprising from about 1 wt. % to about 5 wt. % of glucose, lactose, galactose, or maltose.

47. The sweetener according to any of paragraphs 34 to 46, comprising from about 1 wt. % to about 5 wt. % of sodium chloride or potassium chloride.

48. The sweetener according to any of paragraphs 34 to 47, comprising Rebaudioside A, Rebaudioside B, glucose, and sodium chloride in a weight ratio of 77.55:16.39:3.99: 1.30 respectively.

49. A method to prepare a sweetening composition, comprising one or more steviol glycosides, one or more salts, and one or more natural or synthetic sweeteners.

50. The method according to paragraph 49, wherein the one or more steviol glycosides are selected from steviolbioside, stevioside, rebaudioside A, rebaudioside B, rebaudioside C, rebaudioside D, rebaudioside E, rebaudioside F, rubusoside, dulcoside A, and rebaudioside M.

51. The method according to any of paragraphs 49 to 50, wherein the one or more salts are selected from sodium chloride, potassium chloride, magnesium chloride, sodium sulfate, magnesium sulfate, potassium sulfate, sodium carbonate, potassium carbonate, magnesium carbonate, sodium bicarbonate, and potassium bicarbonate.

52. The method according to any of paragraphs 49 to 51, wherein the one or more natural or synthetic sweeteners are selected from sucrose, fructose, maltose, xylitol, sorbitol, dextrose, glucose, mannitol, aspartame, inulin, sucralose, acesulfame-K, sodium cyclamate, erythritol, thaumatin, arabinose, glatactose, mannose, rhamnose, xylose, trehalose, raffinose, cellobiose, tagatose, DOLCIA PRIMA™ allulose, and mogroside.

53. The method according to any of paragraphs 49 to 52, comprising from about 70 wt. % to about 80 wt. % of Rebaudioside A.

54. The method according to any of paragraphs 49 to 53, comprising from about 10 wt. % to about 20 wt. % of Rebaudioside B.

55. The method according to any of paragraphs 49 to 54, comprising from about 1 wt. % to about 5 wt. % of glucose, lactose, galactose, or maltose.

56. The method according to any of paragraphs 49 to 55, comprising from about 1 wt. % to about 5 wt. % of sodium chloride or potassium chloride.

57. The method according to any of paragraphs 49 to 56, comprising Rebaudioside A, Rebaudioside B, glucose, and sodium chloride in a weight ratio of 77.55:16.39:3.99:1.30 respectively.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

The following blends of steviol glycosides are denoted using the rubric "% Wt1/% Wt2 type1/type2". For instance, "70/30 RA/RB" means a sweetener in which the sweetener content by weight 70% RA and 30% RB by mass. The RA80 ingredient used in the experiments disclosed herein contained approximately 95% total steviol glycosides. The RA50, RA80 and RA97 ingredients used in the experiments were obtained from Sweet Green Fields LLC ("SGF") of Bellingham, Wash.

Example 1

Solubility and Sensory Analysis of RA Hydrolytes

Aim: Determine the solubility and taste attributes of RA50/RA80/RA97 hydrolytes made using differing amounts of reaction reagent.

Materials:

RA50 hydrolyzed using 0.0625/0.125/0.25/0.3125/0.375/0.4375/0.5625/0.625 mL NaOH reagent RA80 hydrolyzed using 0.0625/0.125/0.25/0.3125/0.375/0.4375/0.5625/0.625 mL NaOH reagent RA97 hydrolyzed using 0.0625/0.125/0.25/0.3125/0.375/0.4375/0.5625/0.625 mL NaOH reagent RA50 lot #3020510

RA80 lot #3020526

RA97 lot #3030508

RB lot #032-05-04

Experiment 1a: Solubility of Dried RA50, 80 and 97 Hydrolysates Vs Source Samples: 20% Concentration in Preservative Hypothesis: There is a minimum RB content in a *Stevia* extract below which the *Stevia* extract is rendered relatively insoluble.

1. 1 g of dry RA50 lot #3020510, RA80 lot #3020526, or RA97 lot #3030508 was weighed into a 15 mL screwcap vial.

2. $1/10^{th}$ dilute Vogler preservative was added until powder was dissolved in a final volume of 5 mL at room temp.

3. Screwcap vial was sealed and placed in observation rack.

4. Steps 1-3 were repeated for each of the eight RA50, 80 or 97 samples hydrolyzed using 0.0625/0.125/0.25/0.3125/0.375/0.4375/0.5625/0.625 mL NaOH reagent.

5. All dissolved concentrates were photographed and placed under observation indefinitely.

Experiment 1b: Solubility of RA97 Treated with 0.625 mL Vs Equivalent Blend of RA97/RB Hypothesis: The mere presence of significant amounts of rebaudioside B causes increased apparent solubility of high RA purity *Stevia* extracts.

1. RA97 3030508 and RB were blended to mimic the composition of the RA97 0.625 mL treatment described above.

2. 1 g of RA/RB blend was weighed into a 15 mL screwcap vial.

3. $1/10^{th}$ dilute Vogler preservative was added until powder was fully dissolved in a final volume of 5 mL.

4. Screwcap vial was sealed and placed in observation rack alongside RA97 0.625 mL treatment.

5. RA/RB blend was photographed and placed under observation indefinetly.

6. Sample did not dissolve readily, so RB powder was dried to determine if higher moisture was the cause of insolubility. Dried RB powder consisted of 3.8% moisture.

7. Steps 1-4 were repeated and solubility was not improved.

Experiment 2: Sensory Analysis of RA Source Samples Vs 0.0625/0.3125/0.625 mL Treated Samples 1. 300 ppm samples of RA50#3020510 parent and RA50 0.0625/0.3125/0.625 mL treatments were made in distilled water and tasted blindly by Tester #10 and Tester #11.

2. Scores were recorded using flash sensory profiling sheets

3. Sensory analysis was repeated for RA80#3020526 parent and treated samples

4. Sensory analysis was repeated for RA97#3030508 parent and treated samples

See FIGS. 1-4 for solubility results and FIGS. 5-8 for and sensory analysis of RA Hydrolytes.

Example 2

The sensory effects of hydrolyzed D-Glucose on RA/RB & RA97.

Hypothesis:

The reaction of sodium hydroxide (NaOH) with *Stevia* produces glucose, which causes the brown coloration of liquid concentrates made using this reaction method.

This reaction product enhances the sugar-like sensory attributes of RA/RB, i.e. mouth-feel, body, lower bitterness and improved overall liking.

Materials

RA97 lot #3030508

Rebaudioside B lot #032-05-04

D-Glucose

Distilled $H_2O$

Sodium Hydroxide (NaOH)

Hydrochloric Acid (HCl)

Experiment 1: D-glucose hydrolysis

1. Preheat water bath to 90° C.

2. Dissolve 20 g NaOH in distilled $H_2O$ to reach a final volume of 100 mL, and label as "20% w/v NaOH in $H_2O$"

3. Label 3 separate 50 mL screwcap vials a/b/c and to each add:

0.56 g D-Glucose+39 mL $H_2O$ 0.28 g D-Glucose+39.5 mL $H_2O$ 0.056 g D-Glucose+40 mL $H_2O$ 4. Place all vials in 90° C. preheated water-bath and allow solutions to reach temp 5. In rapid succession, add the following amount of previously made 20% NaOH concentrate to samples a/b/c:
  0.625 mL 20% NaOH Concentrate
  0.3125 mL 20% NaOH Concentrate
  0.0625 mL 20% NaOH Concentrate 6. Heat samples for 2 hours in 90° C. water bath 7. After 2 hours of heating, remove vials from the water bath and allow samples to cool to room temperature. Take pictures of the samples upon removal for coloration recording.

iii. 300 mg RA/RB blend+ distilled $H_2O$ to a final volume of 1,000 mL (300 ppm RA/RB).

b. Set 2
  i. 299.04 mg RA97+668.5 μL D-Glucose solution vial A+ distilled $H_2O$ to a final volume of 1,000 mL (299.04 ppm RA97+9.6 ppm reacted glucose).
  ii. 299.52 mg RA97+668.5 μL D-Glucose solution vial B+ distilled $H_2O$ to a final volume of 1,000 mL (299.04 ppm RA97+4.8 ppm reacted glucose).
  iii. 300 mg RA97+ distilled $H_2O$ to a final volume of 1,000 mL (300 ppm RA97).

Each set was tasted using double-blind Flash sensory analysis (number of analysts=2).

TABLE 1

Double-blind taste results (T = Tester)

| Set 1 | T#10 Sweetness | T#11 Sweetness | T#10 Bitter | T#11 Bitter | T#10 Linger | T#11 Linger | T#10 Sugar Like Body | T#11 Sugar Like Body | T#11 Dry | T#10 Ov. Like | T#11 Ov. Like |
|---|---|---|---|---|---|---|---|---|---|---|---|
| RA/RB +A | 6.6 | 6 | 1 | 2.5 | 2.7 | 5.5 | 5 | 5 | 3.8 | 7 | 8 |
| RA/RB +B | 6.6 | 6 | 1 | 3.5 | 2.7 | 5.5 | 4.5 | 4.5 | 3.8 | 6 | 6.8 |
| RA/RB Control | 6.6 | 6 | 2 | 6 | 3 | 5.5 | 4.5 | 4.5 | 7 | 6 | 6 |
| Set 2 | | | | | | | | | | | |
| RA97 +A | 6.5 | 6.8 | 1.2 | 5 | 5 | 5 | 5.1 | 5.9 | 4.5 | 7 | 7.2 |
| RA97 +B | 6.5 | 6.8 | 1.2 | 5 | 5 | 5 | 5.1 | 4.9 | 5.5 | 7 | 6.8 |
| RA97 Control | 5.8 | 6.8 | 2.3 | 5 | 5 | 5 | 3.2 | 4.4 | 5.9 | 6 | 6.8 |

8. Take pH of room temperature samples and record. If samples are not at a target pH of ~7.4, neutralize them to target using a 1M solution of HCl Experiment 2: Testing the sensory effects of hydrolyzed D-glucose on RA/RB and RA97

1. To replicate the composition of a dried RA/RB hydrolyte treated with 0.625 mL of reagent, 5 g of RA/RB using a 61:39 ratio of RA97:RB was prepared, making sure to mix the sample thoroughly to ensure homogenization. (3.05 g RA97+1.95 g RB=5 g RA/RB blend). This mixture was a replica of the RA97 treated sample where 0.625 mL NaOH had been added. HPLC was used to confirm replication.

2. The amount of liquid D-glucose from each vial to be equivalent to 0.96 mg D-glucose from vial A/0.48 mg reacted D-glucose from vial B (representing the reaction product from use of 300 ppm of Stevia reacted with the highest and mid-level amount of 20% NaOH (0.625 mL and 0.3215 mL respectively) would be:
  X=microliters of reacted D-glucose liquid
  14.36 mg/1000 μl=0.96 mg/X μl
  14.36 X=0.96*1000
  X=960/14.36
  X=66.85 μl=0.96 mg reacted glucose from vial A for a 100 mL test beverage and 0.48 mg reacted glucose from vial B.

3. The following solution sets were created:
a. Set 1
  i. 299.04 mg RA/RB blend+668.5 μL D-Glucose solution vial A+ distilled $H_2O$ to a final volume of 1,000 mL (299.04 ppm RA/RB+9.6 ppm reacted glucose).
  ii. 299.52 mg RA/RB blend+668.5 μL D-Glucose solution vial B+ distilled $H_2O$ to a final volume of 1,000 mL (299.52 ppm RA/RB+4.8 ppm reacted glucose).

SUMMARY

Figure 9:
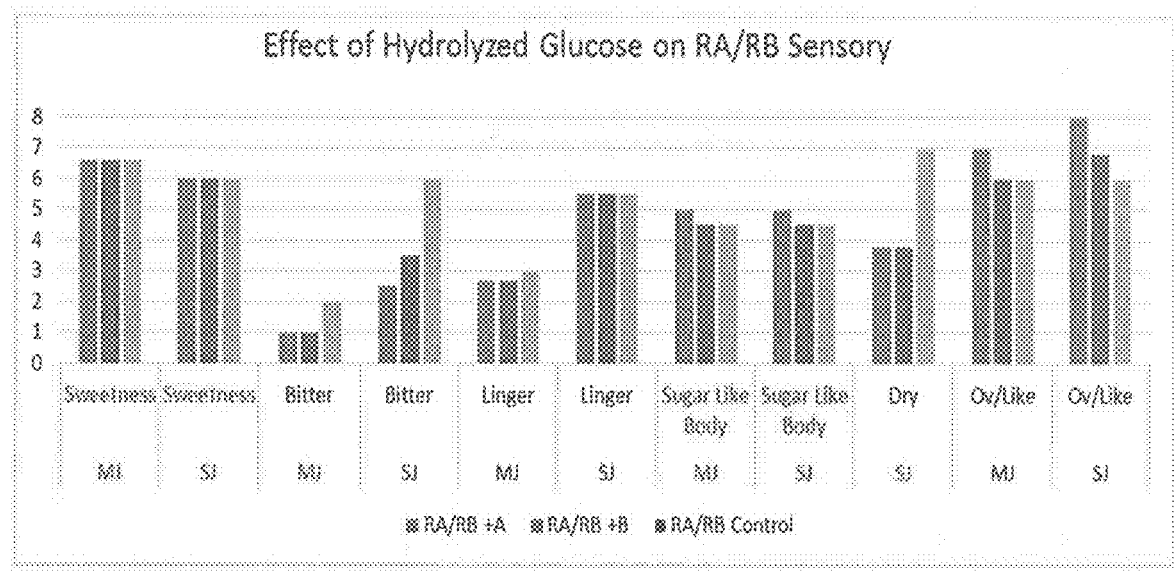
FIG. 9: A graphical illustration showing the effect of hydrolyzed glucose on RA/RB sensory (MJ=Tester #10, SJ=Tester #11).
Figure 10:
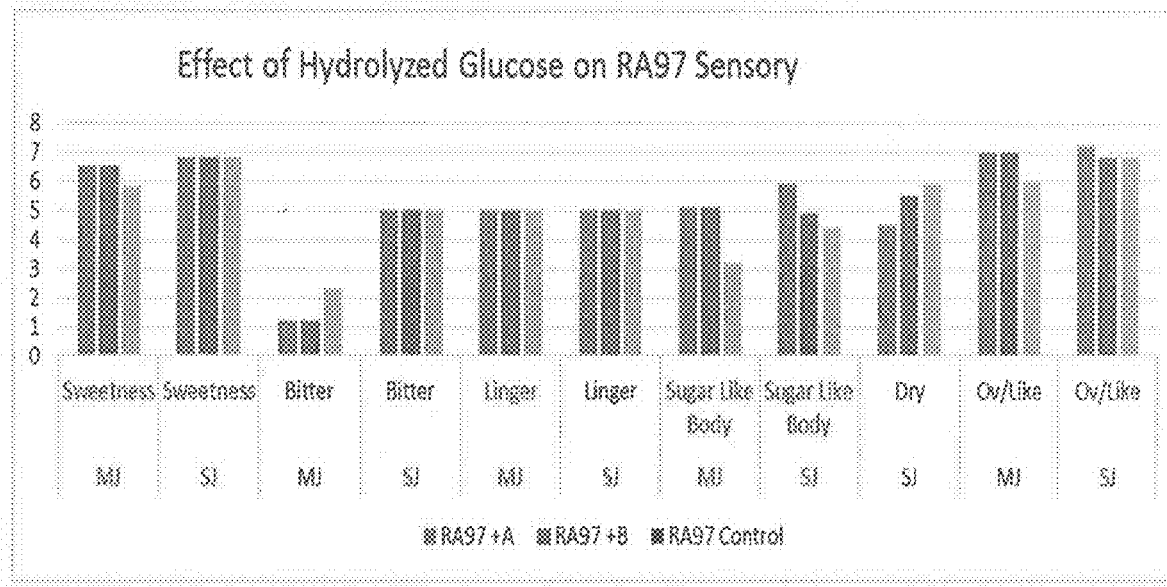
FIG. 10: A graphical illustration showing the effect of hydrolyzed glucose on RA97 sensory (MJ=Tester #10, SJ=Tester #11).

All samples appeared to be iso-sweet (FIGS. 9 and 10).

In the RA/RB samples (Set 1), addition of hydrolyzed glucose at 9.6 or 4.8 ppm appeared to:

1. Reduced bitterness.

2. Have no effect on lingering

3. Increase sugar-like body

4. Increase overall liking.

In the RA97 samples (Set 2), addition of hydrolyzed glucose at 9.6 or 4.8 ppm appeared to:

1. Very slightly reduce bitterness.

2. Have no effect on lingering

3. Increase sugar-like body

4. Increase overall liking.

Conclusions:

The glucose hydrolysate appears to be acting as a flavor. At the concentration used, it likely has no functional sweetness, which was evidenced in the sweetness ratings. The sensory work was done completely blind and with sample order randomized. Even at the low concentrations used, the sample containing 10 ppm glucose hydrolysate was easily discernible. Even though at these low concentrations the hydrolyzed glucose acted as a flavor, the next step is to increase the concentration to determine whether at the maximum potential hydrolyzed glucose concentration (calculated at about 42 ppm or 0.042% for the highest degree of hydrolysis) has negative sensory effects.

Example 3

Iso-Sweet and Preference Testing for Hydrolysed *Stevia* (equivalent to a commercial cranberry juice having 83:17 RA/RB blend).

Aim 1: Determine via HPLC which RA97 hydrolysis material and which RA80 hydrolysis material is closest compositionally in terms of RA to RB ratio with commercial cranberry juice having 83:17 RA/RB blend.

Aim 2: Determine via sensory analysis what ppm level of equivalent RA97 hydrolysis material and RA 80 hydrolysis material is iso-sweet with commercial cranberry juice having 83:15 RA/RB blend in a 9% sugar base.

Aim 3: Determine via sensory analysis if any other treatment level of RA97/RA80 hydrolysis material are more preferred than the iso-sweet hydrolysis materials of RA97/RA80 or commercial fruit drink 83:15 RA/RB blend in a 9% sugar base Materials
RA100 SGF lot #3020604
RB 032-05-04
RA80 Hydrolysis product using 0.125 mL level of treatment (RA80-H.125)
RA80 Hydrolysis product using 0.3125 mL level of treatment (RA80-H.3125)
RA80 Hydrolysis product using 0.625 mL level of treatment (RA80-H.625)
RA97 Hydrolysis product using 0.125 mL level of treatment (RA97-H.125)
RA97 Hydrolysis product using 0.3125 mL level of treatement (RA97-H.3125)
RA97 Hydrolysis product using 0.625 mL level of treatment (RA97-H.625)
White Granulated Sucrose
Distilled Reverse Osmosis Water

Experiment 1: Composition Comparison and Selection

All samples of RA97 and RA80 hydrolysis material were compared to 83:17 RA100/RB blend. The samples that were closest in composition were the 0.125 mL reagent treated RA97 (RA97-H.125) and RA80 (RA80-H.125) samples.

Figure 11:
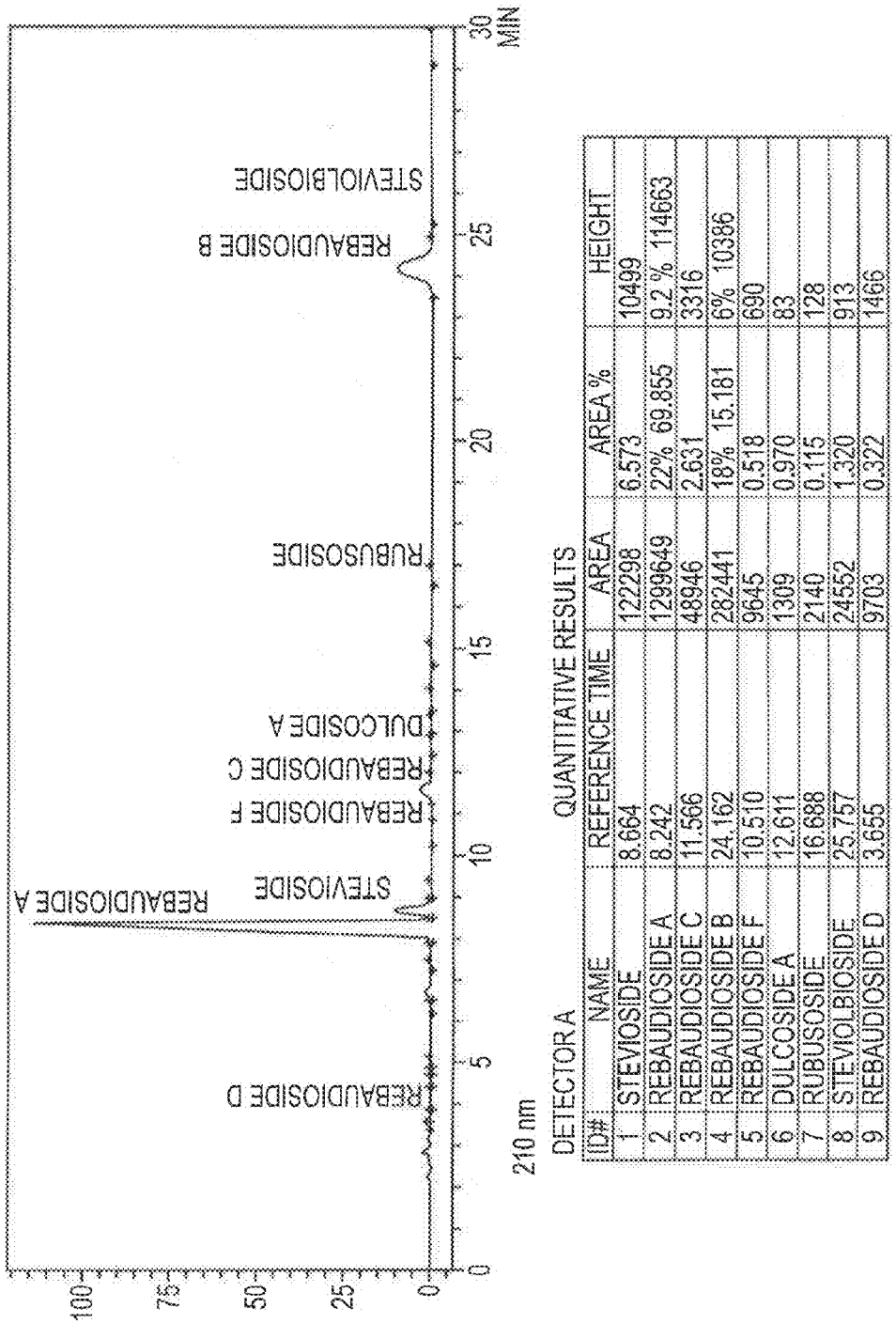
FIG. 11: A HPLC chromatogram of hydrolyzed 83/17 RA/RB dry blend.
Figure 12:
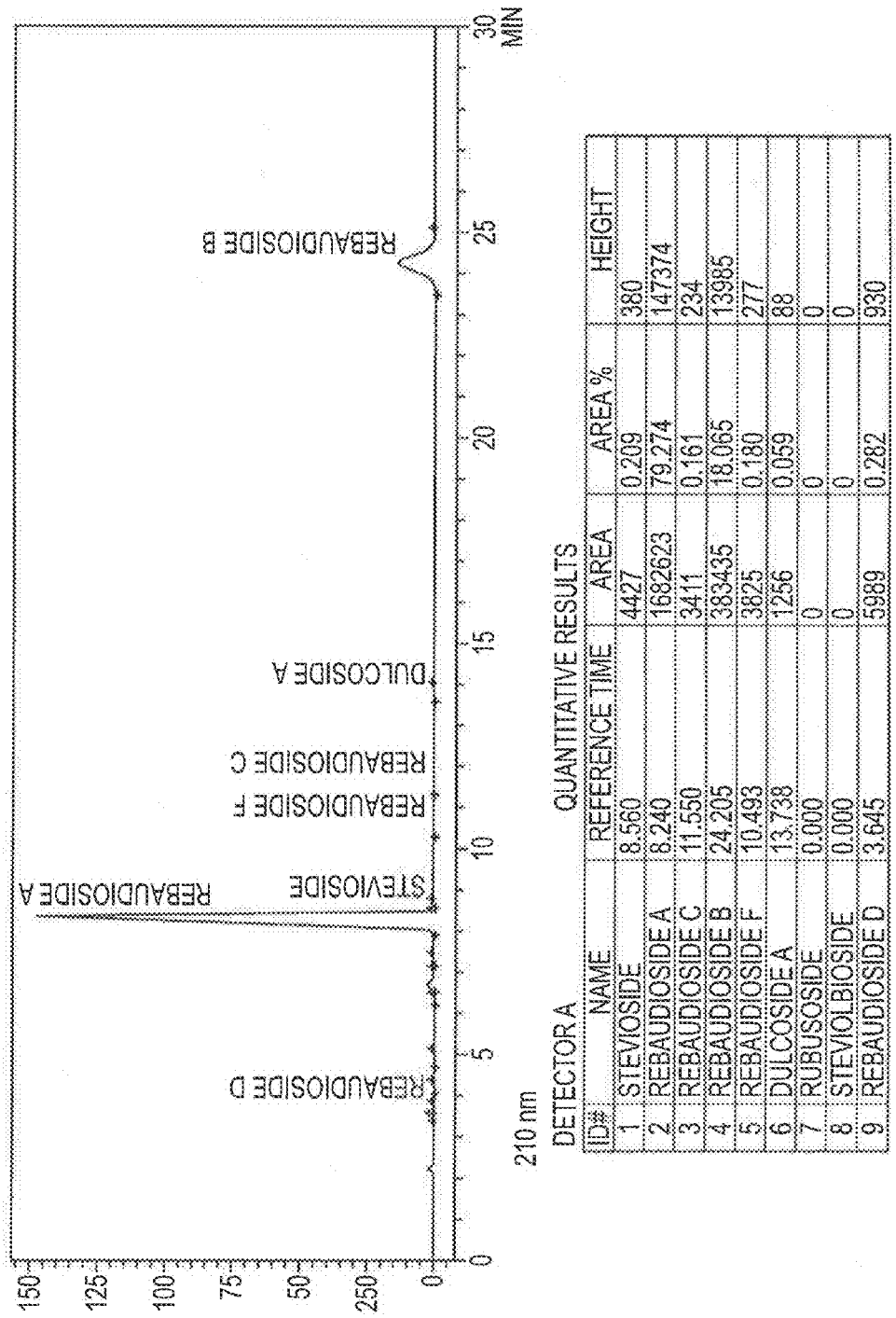
FIG. 12: A HPLC chromatogram of hydrolyzed RA80.
Figure 13:
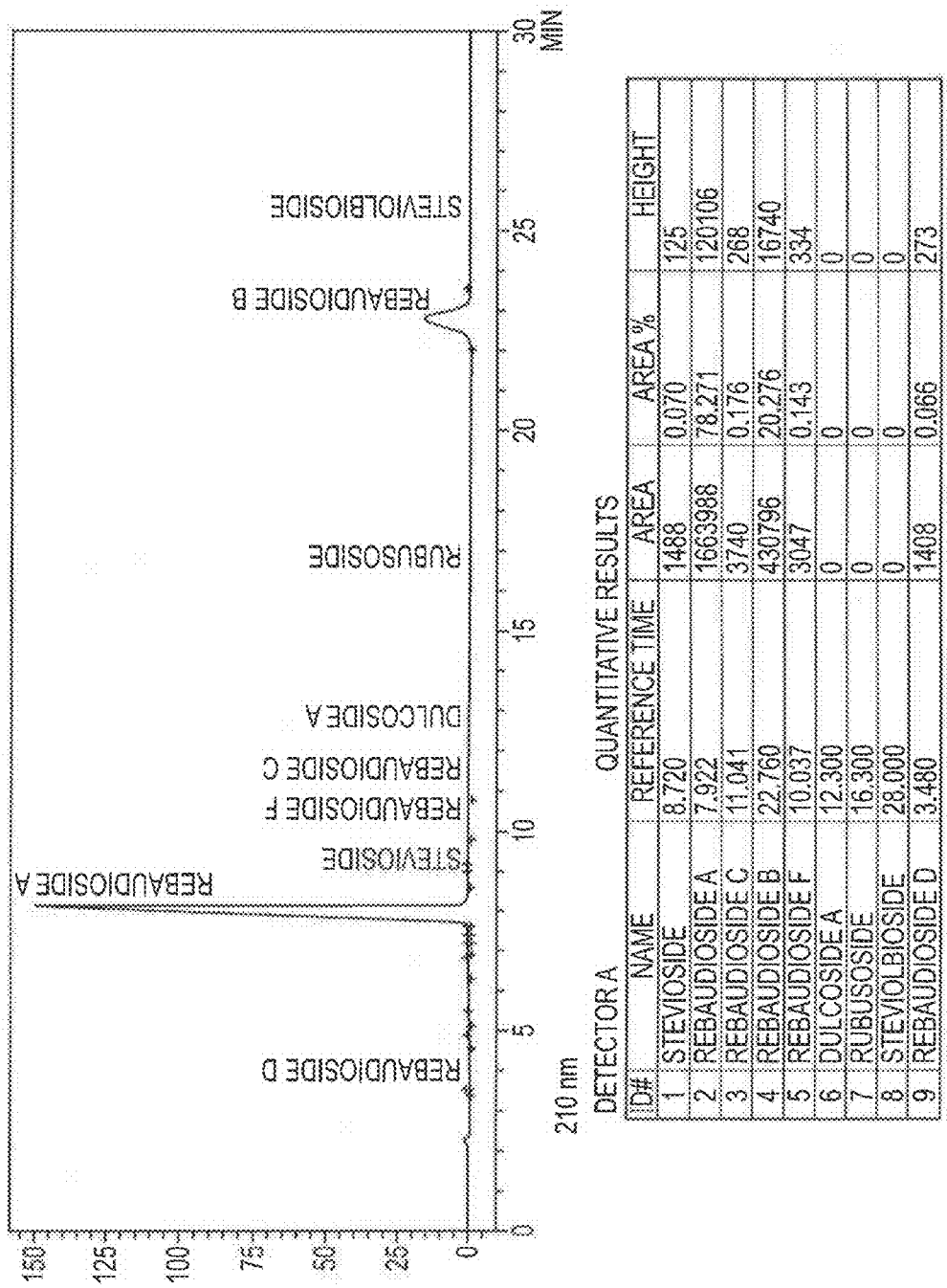
FIG. 13: A HPLC chromogram of hydrolyzed RA97.
Figure 14:
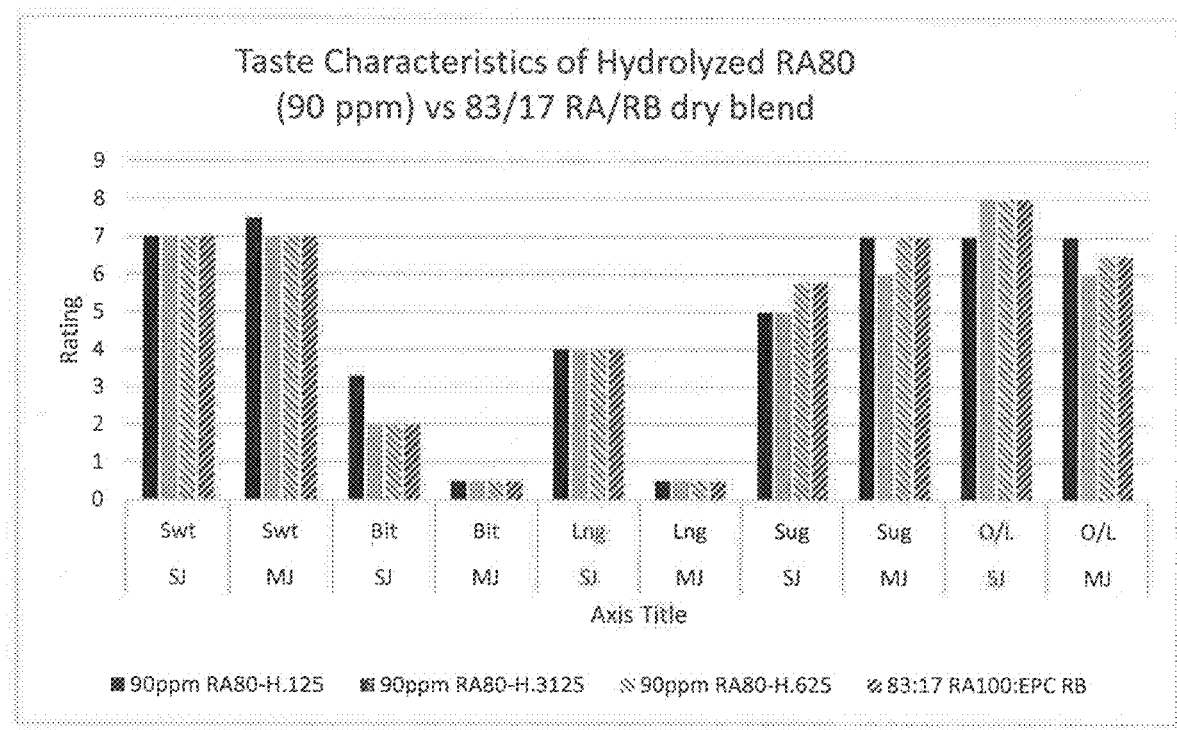
FIG. 14: A graphical illustration showing the taste characteristics of hydrolyzed RA80 (90 ppm) vs 83/17 RA/RB dry blend (MJ=Tester #10, SJ=Tester #11).
Figure 15:
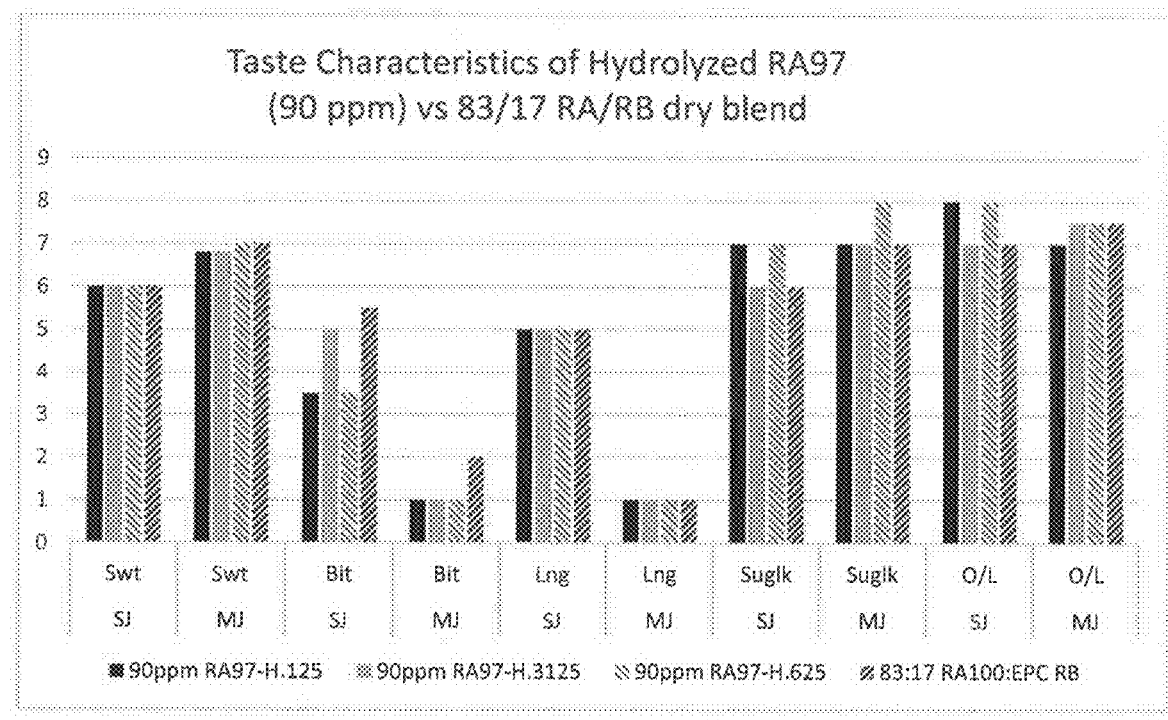
FIG. 15: A graphical illustration showing the taste characteristics of hydrolyzed RA97 (90 ppm) vs 83/17 RA/RB dry blend (MJ=Tester #10, SJ=Tester #11).

HPLC chromatograms of the dry blend and RA80 and 97 hydrolyzed products are shown in FIGS. 11-13.

Experiment 2: Iso-Sweet Sensory Test

Both RA97-H.125 & RA80-H.125 were tested against known control 83:17 RA/RB blend in a 9% sucrose water base samples were double blinded and tested n=2 using flash sensory scales. After testing the iso-sweet was determined to be closest at 90 ppm, the same level found in a commercial cranberry juice.

TABLE 2

Iso-sweet sensory test results A

| Sample | Sample (Q.S to 500 mL) Description | Tester #12 Sweetness | Tester #13 Sweetness |
|---|---|---|---|
| 736 | 70 ppm RA97-H.125 | 4.4 | 4.8 |
| 591 | 90 ppm RA97-H.125 | 5 | 4 |
| 188 | 110 ppm RA97-H.125 | 5.6 | 6 |
| 905 | 130 ppm RA97-H.125 | 5.9 | 5.2 |
| control | 83:17 RA100:RB blend | 5 | 5 |

TABLE 3

Iso-sweet sensory test results B

| Sample | Sample (Q.S to 500 ml) Description | Tester #12 Sweetness | Tester #13 Sweetness |
|---|---|---|---|
| 460 | 70 ppm RA80-H.125 | 4.2 | 4.6 |
| 568 | 90 ppm RA80-H.125 | 5 | 4.5 |
| 633 | 110 ppm RA80-H.125 | 5.5 | 5 |
| 789 | 130 ppm RA80-H.125 | 6.4 | 5.5 |
| control | 83:17 RA100:RB blend | 5 | 5 |

To determine if a hydrolyzed RA product had similar taste characteristics to an 83/17 dry blend of RA100 and RB, 90 ppm concentration in 9% (w/w) sugar water (cold) were compared using flash sensory to the 83/17 dry blend. Samples were tasted double blind and sample order was randomized. The results are shown in Table 4.

TABLE 4

Taste characteristics of hydrolyzed RA80 (90 ppm) vs 83/17 RA/RB blend (see FIG. 11)

| Sample | Sample (Q. S to 500 ml) Description | T11 Swt | T10 Swt | T11 Bit | T10 Bit | T11 Lng | T10 Lng | T11 Sug | T10 Sug | T11 O.L. | T10 O.L. |
|---|---|---|---|---|---|---|---|---|---|---|---|
| 883 | 90 ppm RA80-H.125 | 7 | 7.5 | 3.3 | 0.5 | 4 | 0.5 | 5 | 7 | 7 | 7 |
| 315 | 90 ppm RA80-H.3125 | 7 | 7 | 2 | 0.5 | 4 | 0.5 | 5 | 6 | 8 | 6 |
| 997 | 90 ppm RA80-H.625 | 7 | 7 | 2 | 0.5 | 4 | 0.5 | 5.8 | 7 | 8 | 6.5 |
| 472 | 83:17 RA100:RB | 7 | 7 | 2 | 0.5 | 4 | 0.5 | 5.8 | 7 | 8 | 6.5 |

Conclusions: Overall there appeared to no marked difference between samples.

TABLE 5

Taste characteristics of hydrolyzed RA97 (90 ppm) vs 83/17 RA/RB blend (see FIG. 12)

| Sample | Sample (Q. S to 500 ml) Description | T11 Swt | T10 Swt | T11 Bit | T10 Bit | T11 Lng | T10 Lng | T11 Sug | T10 Sugl | T11 O.L. | T10 O.L. |
|---|---|---|---|---|---|---|---|---|---|---|---|
| 883 | 90 ppm RA97-H.125 | 6 | 6.8 | 3.5 | 1 | 5 | 1 | 7 | 7 | 8 | 7 |
| 315 | 90 ppm RA97-H.3125 | 6 | 6.8 | 5 | 1 | 5 | 1 | 6 | 7 | 7 | 7.5 |
| 997 | 90 ppm RA97-H.625 | 6 | 7 | 3.5 | 1 | 5 | 1 | 7 | 8 | 8 | 7.5 |
| 472 | 83:17 RA100:RB | 6 | 7 | 5.5 | 2 | 5 | 1 | 6 | 7 | 7 | 7.5 |

Conclusions: There are no marked differences between sample taste profiles. The only relatively consistent difference was the apparent reduction in bitterness.

Example 4

The samples in lines 2, 4, and 8 of FIG. 1 (0.0625, 0.25, and 0.5625 20% NaOH added) were prepared by mixing raw materials and then formulated in to solutions.

Test 1

TABLE 6

Sample formulations for taste profiling

| Sample # | RA (ppm) | RB (ppm) | Glucose (ppm) | NaCl (ppm) | Sample # |
|---|---|---|---|---|---|
| 1-1 | 202 | 76 | 17 | 5.5 | 1-1 |
| 1-2 | 202 | 76 | — | — | 1-2 |
| 2-1 | 155 | 112 | 25 | 8 | 2-1 |
| 2-2 | 155 | 112 | — | — | 2-2 |
| 3-1 | 85 | 165 | 37 | 12 | 3-1 |
| 3-2 | 85 | 165 | — | — | 3-2 |

TABLE 7

Test results of taste profiling

| Sample # | Sugar like | Bitterness | Aftertaste | Lingering | Sugar like |
|---|---|---|---|---|---|
| 1-1 | 3 | 1 | 2 | 4 | 3 |
| 1-2 | 3 | 1 | 2 | 4 | 3 |
| 2-1 | 4 | 0 | 0 | 2 | 4 |
| 2-2 | 3 | 1 | 2 | 4 | 3 |
| 3-1 | 4 | 0.5 | 1 | 2 | 4 |
| 3-2 | 4 | 0.5 | 2 | 2 | 4 |

The results showed that for sample 1-1 and sample 1-2, the concentrations of both glucose and salt were relative low and the difference between the samples was not significant; for sample 2-1 and sample 2-2 the concentrations of both glucose and salt were higher than sample 1-1 and 1-2, and the difference between the samples was significant; for sample 3-1 and sample 3-2 the concentration of RB in the product was high, lowing the overall sweetness. The difference between the samples was not significant.

Test 2

Hydrolysis product: Lot #15-0100, comprising RA 77.55%, RB 16.39%, Glucose 3.99%, and NaCl 1.30%.

Mixed product: prepared by simply mixing raw materials according to the ratio of Lot #15-0100.

TABLE 8

Sample formulations for taste profiling

| Sample No. | RA (ppm) | RB (ppm) | Glucose (ppm) | NaCl (ppm) |
|---|---|---|---|---|
| 4-1 | 384 | 89 | 20 | 6.5 |
| 4-2 | 384 | 89 | — | — |
| 4-3 | 384 | 89 | 20 | — |
| 4-4 | 384 | 89 | — | 6.5 |
| 4-5 | Lot#15-0100 500 ppm | | | |

TABLE 9

Test results of taste profiling

| Sample No. | Sugar like | Bitterness | Aftertaste | Lingering |
|---|---|---|---|---|
| 4-1 | 4 | 0 | 0.5 | 2 |
| 4-2 | 3.5 | 1 | 2 | 4 |
| 4-3 | 4 | 0 | 1 | 2 |
| 4-4 | 3.5 | 0 | 0.5 | 2 |
| 4-5 | 4 | 0 | 0.5 | 2 |

The results showed that there is no difference in taste profile between the products prepared by hydrolysis and that prepared by simply mixing. The addition of glucose and salt improved the taste profile significantly, wherein glucose improved the "sugar like" profile, and salt improved the "aftertaste" profile, both the two components had positive effects on the taste profile.

Example 5

Sample 1 was prepared according to the below hydrolysis process and the content of each component was analyzed. Another sample (Sample 2), which has the same component as Sample 1, was formulated by simply blending the raw materials. A control sample, which has the same RA and RB content but does not contain any salt or additional sweetener, was prepared by simply blending the raw materials. The taste profile of the three samples were evaluated.

Preparation of Sample 1

10 grams of RA97 was dissolved in deionized water and 1.56 mL of 20% NaOH was added. The mixture was heated to 90° C. for 8 h with stirring. The resultant mixture was then cooled, neutralized to pH 7.0 with dilute hydrochloric acid, and spray dried to afford the final product as a yellowish powder.

Test Result

| | |
|---|---|
| RA | 20.7% |
| RB | 61.2% |
| NaCl | 4.4% |
| Glucose | 13.7% |

The product was formulated into 300 ppm solution with deionized water. The concentration of each component was:

| | |
|---|---|
| RA | 20.7% × 300 ppm = 62.1 ppm |
| RB | 61.2% × 300 ppm = 18.4 ppm |
| NaCl | 4.4% × 300 ppm = 1.3 ppm |
| Glucose | 13.7% × 300 ppm = 41.1 ppm |

Preparation of Sample 2

Sample 2 was prepared and formulated into 300 ppm solution, with RA, RB, NaCl, and glucose.

| | |
|---|---|
| RA | 62.1 ppm |
| RB | 18.4 ppm |
| NaCl | 1.3 ppm |
| Glucose | 41.1 ppm |

Preparation of Control Sample

Control sample was prepared and formulated into solution with RA and RB.

| | |
|---|---|
| RA | 62.1 ppm |
| RB | 18.4 ppm |

Select sensory taste profiles of these three solution were evaluated, and the results were summarized below.

TABLE 10

Taste profiles of samples

| Sample | Sugar like | Bitterness | Aftertaste | Lingering |
|---|---|---|---|---|
| Sample 1 | 4 | 0.5 | 0.5 | 2 |
| Sample 2 | 4 | 0.5 | 0.5 | 2 |
| Control | 3.5 | 2 | 1.5 | 3 |

The results showed that there is no difference between Sample 1 and Sample 2, demonstrating that the taste profile was determined by composition per se, regardless of the preparation process. The results showed that there is significant difference between Sample 1 or Sample 2 and control sample, demonstrating that combination of RA, RB, glucose and salts can improve the sensory profile (i.e. in this experiment sugar like, bitterness, aftertaste, and lingering) of a sweetening composition.

Example 6

A composition according to the present invention was prepared from RA100 as shown in Table 11.

TABLE 11

RA100 Compositions

| Sample No. | RA100 | mls 1% NaOH added | g NaOH added | g glucose potentially produced | % RA | % RB | % SS | % Total glycoside |
|---|---|---|---|---|---|---|---|---|
| 140-35-01 | 10 g | 3.125 | 0.03125 | 0.14 | 90.87 | 6.66 | 0.19 | 97.72 |
| 140-35-02 | 10 g | 31.25 | 0.3125 | 1.4 | 37.66 | 47.18 | 0.15 | 84.99 |

The RA composition in Table 11 were prepared into solutions in Table 12.

TABLE 12

RA100 Solutions

| Sample No. | RA | RB | Glucose | NaCl |
|---|---|---|---|---|
| 1 | | | 140-35-01 500 ppm | |
| 2 | 454 ppm | 33 ppm | — | — |
| 3 | | | 140-35-02 500 ppm | |
| 4 | 188 ppm | 236 ppm | | |

Sensory profiles were taken and are shown in Table 13 and Table 14.

TABLE 13

Evaluation results for sample 1 and 2.

| Sample No. | Sugar like | Bitterness | Aftertaste | Lingering |
|---|---|---|---|---|
| 1 | 3.5 | 1 | 2 | 3 |
| 2 | 3 | 2 | 3 | 3 |

Result: The concentrations of glucose and salt in the product are low, since a relative small amount of NaOH was added. The taste profile of the product is improved in comparison with a similar composition without glucose and salt.

TABLE 14

Evaluation results for sample 3 and 4.

| Sample No. | Sugar like | Bitterness | Aftertaste | Lingering |
|---|---|---|---|---|
| 3 | 4 | 0 | 0.5 | 2 |
| 4 | 3 | 1 | 3 | 3 |

Result: The taste profile of the composition according to the present invention is significantly improved in comparison with a control sample without glucose and salt.

Example 7

Evaluation of the effects of other sweeteners and inorganic salts on the taste profile of the composition.

Test 1: Evaluation of Compositions Comprising Sodium Chloride and Potassium Chloride

TABLE 15

Solutions for evaluation

| Sample No. | RA | RB | NaCl | KCl |
|---|---|---|---|---|
| 309 | 384 ppm | 89 ppm | — | — |
| 517 | 384 ppm | 89 ppm | 6.5 ppm | — |
| 273 | 384 ppm | 89 ppm | — | 6.5 ppm |

TABLE 16

Evaluation results

| Sample No. | Sugar like | Bitterness | Aftertaste | Lingering |
|---|---|---|---|---|
| 309 | 3.5 | 1 | 2 | 4 |
| 517 | 4 | 0 | 1 | 2 |
| 273 | 4 | 0 | 0.5 | 2 |

Results: Substantially same results were achieved with potassium chloride and sodium chloride.

Test 2: Evaluation of Compositions Comprising Various Sweeteners

TABLE 17

Solutions for evaluation

| Sample No. | RA | RB | Sweetener |
|---|---|---|---|
| 724 | 384 ppm | 89 ppm | Glucose (20 ppm) |
| 136 | 384 ppm | 89 ppm | Fructose (20 ppm) |
| 507 | 384 ppm | 89 ppm | Lactose (20 ppm) |
| 302 | 384 ppm | 89 ppm | Galactose (20 ppm) |
| 109 | 384 ppm | 89 ppm | Maltose (20 ppm) |

TABLE 18

Evaluation results

| Sample No. | Sugar like | Bitterness | Aftertaste | Lingering |
|---|---|---|---|---|
| 724 | 4 | 0 | 1 | 2 |
| 136 | 3.5 | 1 | 1 | 2 |
| 507 | 4.5 | 0 | 0 | 1 |
| 302 | 4 | 0 | 1 | 2 |
| 109 | 4 | 0 | 0 | 2 |

Results: The effect of fructose was slightly lower than glucose, and those of lactose, galactose, and maltose were similar or even better than glucose. The taste profiles of the compositions with an additional sweetener were significantly improved in comparison to that without an additional sweetener (sample 309 in test 1).

Example 8

Evaluation of salt on the taste profile.

Test I: Evaluation of various salts on the taste profile of compositions without glucose.

TABLE 19

Solution for evaluation

| Sample No. | Salt | RA | RB | Salt |
|---|---|---|---|---|
| 327 | NaCl | 384 ppm | 89 ppm | 6.5 ppm |
| 782 | $Na_2CO_3$ | 384 ppm | 89 ppm | 6.5 ppm |
| 509 | $K_2CO_3$ | 384 ppm | 89 ppm | 6.5 ppm |

TABLE 20

Evaluation result

| Sample No. | Sugar like | Bitterness | Aftertaste | Lingering |
|---|---|---|---|---|
| 327 | 4 | 0 | 1 | 2 |
| 782 | 3.5 | 1 | 2 | 2 |
| 509 | 3.5 | 1 | 1.5 | 2 |

The addition of carbonates to the composition may result in an "alkaline" (bitterness, astringent, and soapy) taste. Carbonates can also carbonate the composition and can result in a "soda like" taste.

Test II: Evaluation of various salts on the taste profile of composition according to the present invention with glucose.

TABLE 21

Solution for evaluation

| Sample No. | Salt | RA | RB | Salt | Glucose |
|---|---|---|---|---|---|
| 327 | NaCl | 384 ppm | 89 ppm | 6.5 ppm | 20 ppm |
| 782 | $Na_2CO_3$ | 384 ppm | 89 ppm | 6.5 ppm | 20 ppm |
| 509 | $K_2CO_3$ | 384 ppm | 89 ppm | 6.5 ppm | 20 ppm |

TABLE 22

| Sample No. | Sugar like | Bitterness | Aftertaste | Lingering | Sample No. |
|---|---|---|---|---|---|
| 327 | 4 | 0 | 0 | 2 | 327 |
| 782 | 3.5 | 0 | 1.5 | 2 | 782 |
| 509 | 3.5 | 0 | 1.5 | 2 | 509 |

Glucose may mask the "bitterness" taste of carbonates, however as shown, the aftertaste improvement can be significant.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for sweetening a target composition, comprising the step of:
    adding to the target composition an effective amount of a sweetener composition comprising rebaudioside A, rebaudioside B, one or more salts, and one or more natural or synthetic sweeteners,
    wherein rebaudioside A comprises 70-80 wt. % of the sweetener composition,
    wherein rebaudioside B comprises 10-20 wt. % of the sweetener composition,
    wherein the one or more salts comprises 0.1-5 wt. % of the sweetener composition, and
    wherein the one or more natural or synthetic sweeteners comprise 1-10 wt. % of the sweetener composition and is not a rebaudioside,
    wherein the one or more salts are selected from the group consisting of sodium chloride, potassium chloride, magnesium chloride, sodium sulfate, magnesium sulfate, potassium sulfate, sodium carbonate, potassium carbonate, magnesium carbonate, sodium bicarbonate, potassium bicarbonate, and any combination thereof, and
    wherein the one or more natural or synthetic sweeteners are selected from the group consisting of sucrose, fructose, maltose, lactose, xylitol, sorbitol, dextrose, glucose, mannitol, aspartame, sucralose, acesulfame-K, sodium cyclamate, inulin, erythritol, thaumatin, arabinose, galactose, mannose, rhamnose, xylose, trehalose, raffinose, cellobiose, tagatose, allulose, mogroside, and any combination thereof.

2. The method of claim 1, wherein the sweetener composition has increased solubility compared to the same composition without the one or more salts and/or the one or more natural or synthetic sweeteners.

3. The method of claim 1, wherein the sweetener composition has an improved aftertaste compared to the same composition without the one or more salts and/or the one or more natural or synthetic sweeteners.

4. The method of claim 1, wherein the sweetener composition comprises rebaudioside A, rebaudioside B, glucose, and sodium chloride.

5. The method of claim 1, wherein the sweetener composition further comprises one or more steviol glycosides selected from the group consisting of steviolbioside, stevioside, rebaudioside C, rebaudioside D, rebaudioside E, rebaudioside F, rubusoside, dulcoside A, and rebaudioside M.

6. The method of claim 5, wherein the sweetener composition comprises rebaudioside M.

7. The method of claim 5, wherein the sweetener composition comprises rebaudioside D and rebaudioside M.

8. The method of claim 7, wherein the one or more steviol glycosides comprise 1.9 wt. % or less of the sweetener composition.

9. The method of claim 1, wherein the target composition is a beverage.

10. The method of claim 1, wherein the target composition is a food preparation.

11. A method for sweetening a target composition, comprising the step of:
    adding to the target composition an effective amount of a sweetener composition comprising,
    rebaudioside A in an amount of 70-80 wt. % of the sweetener composition;
    rebaudioside B in an amount of 10-20 wt. % of the sweetener composition,
    glucose in an amount of 1-10 wt. % of the sweetener composition; and
    sodium chloride in an amount of 0.1-5 wt. % of the sweetener composition.

12. The method of claim 11, wherein the sodium chloride comprises greater than 0.1 wt. % of the composition, but less than or equal to 0.5 wt. % of the sweetener composition.

13. The method of claim 11, wherein the mole ratio of rebaudioside B and glucose is about 1:1.

14. The method of claim 11, wherein the sweetener composition further comprises one or more steviol glycosides selected from the group consisting of steviolbioside, stevioside, rebaudioside C, rebaudioside D, rebaudioside E, rebaudioside F, rubusoside, dulcoside A, and rebaudioside M.

15. The method of claim 14, wherein the sweetener composition comprises rebaudioside M.

16. The method of claim 14, wherein the sweetener composition comprises rebaudioside D and rebaudioside M.

17. The method of claim 14, wherein the one or more steviol glycosides comprise 1.9 wt. % or less of the sweetener composition.

18. The method of claim 11, wherein the target composition is a beverage.

19. The method of claim 11, wherein the target composition is a food preparation.

* * * * *